US011272859B1

(12) United States Patent
Badee et al.

(10) Patent No.: US 11,272,859 B1
(45) Date of Patent: *Mar. 15, 2022

(54) SYSTEM AND METHOD OF DETERMINING RESPIRATORY STATUS FROM OSCILLOMETRIC DATA

(71) Applicant: Cloud DX, Inc., Brooklyn, NY (US)

(72) Inventors: Vesal Badee, Kitchener (CA); Sara Ross-Howe, Campbellville (CA); Josh Haid, Kitchener (CA); Lamiaa Amzil, Waterloo (CA); Cezar Morun, Kitchener (CA); Bonghun Shin, Waterloo (CA)

(73) Assignee: CLOUD DX, INC., Brooklyn, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/321,812

(22) Filed: May 17, 2021

Related U.S. Application Data

(63) Continuation-in-part of application No. 16/998,361, filed on Aug. 20, 2020, now Pat. No. 11,006,843.

(51) Int. Cl.
*A61B 5/08* (2006.01)
*A61B 5/00* (2006.01)
(Continued)

(52) U.S. Cl.
CPC .......... *A61B 5/0816* (2013.01); *A61B 5/0826* (2013.01); *A61B 5/091* (2013.01);
(Continued)

(58) Field of Classification Search
None
See application file for complete search history.

(56) References Cited

U.S. PATENT DOCUMENTS 5,094,244 A 3/1992 Callahan et al.
5,682,898 A 11/1997 Aung et al.
(Continued)

OTHER PUBLICATIONS

Chen and Chen, "A method for extracting respiratory frequency during blood pressure measurement, from oscillometric cuff pressure pulses and Korotkoff sounds recorded during the measurement" 2016 38th Annual International Conference of the IEEE Engineering in Medicine and Biology Society (EMBC).
(Continued)

*Primary Examiner* — Alex M Valvis
*Assistant Examiner* — Aurelie H Tu
(74) *Attorney, Agent, or Firm* — Stephen E. Zweig

(57) ABSTRACT

A system and method for determining the respiratory and other physiological status of a patient. Here, an oscillometric device is mounted on a patient's limb, and oscillometric pulse waveforms are obtained as the device's cuff deflates, thus obtaining pulse wave signals and artifact signals over multiple patient breaths. A computer processor analyzes these signals, and removes artifacts according to various algorithms. The resulting signal can be viewed as containing both an amplitude modulated envelope of pulse waves (AM signals) and a frequency modulated sequence of pulses at various time intervals (FM signals). The main harmonics of the AM and FM signals contain respiratory status data, and the system analyzes both signals. Breathing depth and even pain data may also be obtained by this method. Artifacts caused by aberrant breathing can be distinguished using non-contact microphones and suitable algorithms. The final respiratory status data is output or stored in memory.

20 Claims, 21 Drawing Sheets

(51) Int. Cl.
    *A61B 5/091*     (2006.01)
    *A61B 7/00*     (2006.01)
    *A61B 5/16*     (2006.01)
    *A61B 5/11*     (2006.01)

(52) U.S. Cl.
    CPC ............ *A61B 5/165* (2013.01); *A61B 5/4824* (2013.01); *A61B 5/6824* (2013.01); *A61B 5/721* (2013.01); *A61B 7/003* (2013.01); *A61B 5/1113* (2013.01); *A61B 2562/0219* (2013.01)

(56) References Cited

U.S. PATENT DOCUMENTS

| | | | |
|---|---|---|---|
| 9,526,458 B2 | 12/2016 | MacAuslan | |
| 10,022,053 B2 | 7/2018 | Li et al. | |
| 10,349,849 B2 | 7/2019 | Knoll | |
| 10,485,449 B2 | 11/2019 | MacAuslan | |
| 11,006,843 B1 * | 5/2021 | Badee | A61B 5/02125 |
| 2003/0163054 A1 | 8/2003 | Dekker | |
| 2009/0278728 A1 * | 11/2009 | Morgan | A61B 5/0816 |
| | | | 342/115 |
| 2012/0302900 A1 * | 11/2012 | Yin | A61B 5/0816 |
| | | | 600/484 |
| 2017/0164850 A1 * | 6/2017 | Murphy | A61B 5/0245 |
| 2017/0273582 A1 | 9/2017 | Kawamoto et al. | |
| 2018/0146926 A1 * | 5/2018 | Ishikawa | A61B 5/721 |

OTHER PUBLICATIONS

Gui et al., "Pulse interval modulation-based method to extract the respiratory rate from oscillometric cuff pressure waveform during blood pressure measurement" Computing in Cardiology (CinC) Sep. 2017—ieeexplore.ieee.org.

Bendall JC, et al. "Prehospital vital signs can predict pain severity: analysis using ordinal logistic regression." Eur J Emerg. Med Dec. 2011;18(6):334-339.

* cited by examiner

Time (arbitrary units) →

Fig. 9

Time (arbitrary units) →

Pulse waveform with motion artifacts

Time (arbitrary units) →

Time (arbitrary units) →

Time (arbitrary units) →

SYSTEM AND METHOD OF DETERMINING RESPIRATORY STATUS FROM OSCILLOMETRIC DATA

CROSS REFERENCE TO RELATED APPLICATIONS

This application is a continuation in part of U.S. patent application Ser. No. 16/998,361, filed Aug. 20, 2020, the entire contents of which are incorporated herein by reference.

BACKGROUND OF THE INVENTION

Field of the Invention

This invention is in the field of breathing rate measurement, respiratory status measurement, oscillometric measurement methods and technology.

Description of the Related Art

Respiration rate (RR), also called "breathing rate", typically expressed in breaths per minute, is an essential but underused vital sign. Jonsdottir et al., in "*Nursing documentation prior to emergency admissions to the intensive care unit*", *Nursing in Critical Care—June* 2011" reports that although respiratory failures are the most common cause of emergency admissions to ICU, nonetheless respiratory rate is one of the least documented vital signs. This problem is due in part to lack of appropriate breathing rate monitoring equipment.

With the recent worldwide COVID-19 pandemic, adequate methods of assessing respiratory system status have become increasingly important. For example, Xu et al., in *Risk factors for* 2019 *novel coronavirus disease (COVID-19) patients progressing to critical illness: a systematic review and meta-analysis, AGING* 2020, Vol. 12, No. 12" reports that elderly male patients with a high respiratory rate (along with high body mass index, and other risk factors) are more likely to develop severe COVID-19 infections.

Although a significant amount of prior art exists covering various automated systems and methods for determining respiration rate, to date, as evidenced by the Jonsdottir study, such methods are still lacking. By contrast, consider oscillometric blood pressure monitors, which are now widely available on a low-cost basis. Oscillometric blood pressure monitors are widely available on a non-prescription basis and are in widespread use for home blood pressure monitoring.

Respiration does have an impact on blood pressure measurements. However, to date, efforts to harness oscillometric techniques for respiration rate monitoring purposes have generally been ineffective. Typically, data from multiple physiological sensors (pulse oximeters, multiple cuff devices, non-oscillometric sensors, ECG sensors) has been needed for such devices to function, and such proposals have generally not been met with commercial success. Thus, further advances in this area would be of significant medical importance.

Previous art on oscillometric monitors equipped with additional physiological sensors, such as ECG and pulse oximetry sensors, includes the work of Li, U.S. Pat. No. 10,022,053, the complete contents of which are incorporated herein by reference.

Other automated breathing sensor art includes Dekker, US 2003/0163054; Callahan U.S. Pat. No. 5,094,244; Aung U.S. Pat. No. 5,682,898; Knoll U.S. Pat. No. 10,349,849; Kawamoto 2017/027358, the complete contents of these are incorporated herein by reference.

Academic work in this area includes the work of Chen and Chen, "*A method for extracting respiratory frequency during blood pressure measurement, from oscillometric cuff pressure pulses and Korotkoff sounds recorded during the measurement*" 2016 38*th Annual International Conference of the IEEE Engineering in Medicine and Biology Society (EMBC)*"; other academic work includes the work of Gui et. al., "*Pulse interval modulation-based method to extract the respiratory rate from oscillometric cuff pressure waveform during blood pressure measurement*" *Computing in Cardiology (CinC)* September 2017—ieeexplore.ieee.org.

Correlation with pain: Other workers (Bendall J C, et. al. "Prehospital vital signs can predict pain severity: analysis using ordinal logistic regression." Eur J Emerg. Med 2011 December; 18(6):334-339) have shown that elevated respiratory rates, heart rate, and systolic pressure are associated with severe pain.

Previous work on computerized methods of using acoustic signals for analyzing coughs and other audible signals of respiratory interruptions and/or distress includes MacAuslan, U.S. Pat. Nos. 9,526,458 and 10,485,449, the entire contents of which are incorporated herein by reference.

BRIEF SUMMARY OF THE INVENTION

Breathing causes relatively small changes in an individual's pulse waves, and oscillometric blood pressure monitoring devices can monitor such pulses. However, these breathing rate induced changes and other such respiratory status changes are relatively small, and are frequently confounded by noise and artifacts in the oscillometric data. The present invention was inspired, in part, by the insight that if a sufficient number of methods to remove artifacts from oscillometric blood pressure monitor data could be found, then it might be possible to employ more aggressive analytical methods to automatically distinguish the subtle breathing rate signals from the oscillometric pulse rate data.

The present invention was also inspired, in part, on the insight that if the faint breathing signal could be distinguished in different ways (e.g., through their impact on multiple characteristics or dimensions on the dominant pulse wave signal), then each different dimension could be used to verify the accuracy of the other dimension. In other words, if the impact of the patient's or user's respiratory rate could be found to impact multiple observable parameters of the underlying pulse rate signal, then the accuracy of the method would be improved. That is, when the different methods were in agreement, the breathing rate results would be more likely to be accurate. When the different rates were not in agreement, the system could report a warning or an error.

In some embodiments, the invention may be a system, device, and method for automatically determining a breathing rate of a patient. This method is based on analyzing pulse waveforms obtained from an oscillometric device mounted on the patient's limb (often on the patient's wrist). This oscillometric device will often comprise a processor (e.g., microprocessor), air pressure generating and release devices, a pressure sensor, and a built-in inflatable cuff configured to go around the patient's limb. The device will often further comprise a display and/or a wireless transceiver (such as a Bluetooth Low Energy transceiver) for displaying the results. The device may optionally also contain a tri-axial (e.g. three-axis) accelerometer. In some embodiments, a wrist-mounted oscillometric device is preferred.

In addition to operating as a standard oscillometric blood pressure monitor, the device also is configured to analyze the pulse waveforms and to determine artifact-free regions of these pulse waveforms. Here various methods may be used, and the artifact-free or at least artifact-reduced areas of the pulse waveforms may be termed edited pulse waveforms.

To obtain multiple dimensions of breathing rate data, the system makes use of the experimental observation that breathing impacts both the amplitude of the individual pulse waves, as well as the time duration between successive pulse waves (e.g., frequency). These show up as changes in the amplitude of the envelope of the pulse wave signals "AM envelope signals" as well as changes in the frequency of the pulses "FM between-pulse-time signals." The invention determines these AM envelope signals and FM between-pulse-time signals and then determines their AM envelope primary harmonics and FM between-pulse-time main harmonics.

The invention then checks to be sure that the AM envelope primary (or main) harmonics and FM between-pulse-time main harmonic are consistent, and if not, may return a warning or error code. However, if the two results meet consistency criteria, the system will then calculate a weighted function of the AM envelope primary harmonics and FM between-pulse-time main harmonics. These results will then be output (or stored in memory) as the patient's breathing rate (respiratory rate) or respiratory status. Alternatively, both AM envelope main harmonics and FM between-pulse-time main harmonics may be used.

Normal breathing is occasionally interrupted by coughing, sneezing, wheezing, or other respiratory interruptions. In some embodiments, as will be discussed, the accuracy of the system may be further improved by utilizing one or microphones to pick up audio data indicative of such respiratory interruptions, and correct the breathing data accordingly. The system may further record when such interruptions were detected, as desired.

In some embodiments, as will be discussed, the pulse wave data may additionally be analyzed to obtain information pertaining to the depth of breathing (e.g., the amount of air being inhaled or exhaled.).

BRIEF DESCRIPTION OF THE DRAWINGS

FIG. 9 shows an example of the data used by the invention's pulse percent residual difference (PRD) motion artifact detection algorithm. In this example, the algorithm is detecting that individual pulses 46 and 47 previously shown in FIG. 8, show low correlation with their neighboring pulses.

FIG. 19 shows an example of some of the inhalation and exhalation characteristics of an FM breathing signal.

DETAILED DESCRIPTION OF THE INVENTION

In this disclosure, the term "breathing rate" is occasionally referred in the alternative as "respiratory status." As used herein, "respiratory status" is intended to be a more general term that, while encompassing "breathing rate", can also encompass other breathing related parameters such as breathing volume (or breathing depth). Note that in this context, breathing interruptions and problems, such as coughing, sneezing, and wheezing, can also impact a patient's respiratory status. Further, other types of physiological stress, such as pain (either acute or chronic), can also impact a patient's respiratory status.

Figure 1:
FIG. 1 shows the invention's wrist-mounted oscillometric device, which unlike prior art devices can also be configured to additionally determine breathing rate data from oscillometric data without use of supplementary physiological sensors such as pulse oximeter or ECG sensors.

FIG. 1 shows an oscillometric device, configured to be mounted on a user's wrist, and configured to also determine breathing rate data (100). Unlike prior art devices, the invention can also be configured to additionally determine breathing rate data from oscillometric data without use of supplementary physiological sensors such as pulse oximeter or ECG sensors. The device contains a plastic enclosure (102), a display (104), control buttons (106) (or the display may be a touch-screen display), and an integrated pressure-cuff (wrist cuff) containing an air bladder (108). Note that the display is showing a pulse rate, systolic and diastolic blood pressure, and also breathing rate in terms of breaths per minute (110).

The high-level mechanical and electrical architectures for the device are illustrated below in FIG. 2 and FIG. 3. Although in some embodiments, the device's electrical circuitry can also support capture of a single lead of Electrocardiography (ECG) and Photoplethysmography (Pulse oximeter or PPG) data for measuring ECG and oxygen saturation ($SpO_2$) as well as pulse wave velocity, an important aspect of the invention is the ability to produce breathing rate information that comes only from one physiological sensor (such as the pressure sensor 122). The use of the accelerometer/gyroscope sensor (202), although present in a preferred embodiment of the invention, is optional.

Figure 2:
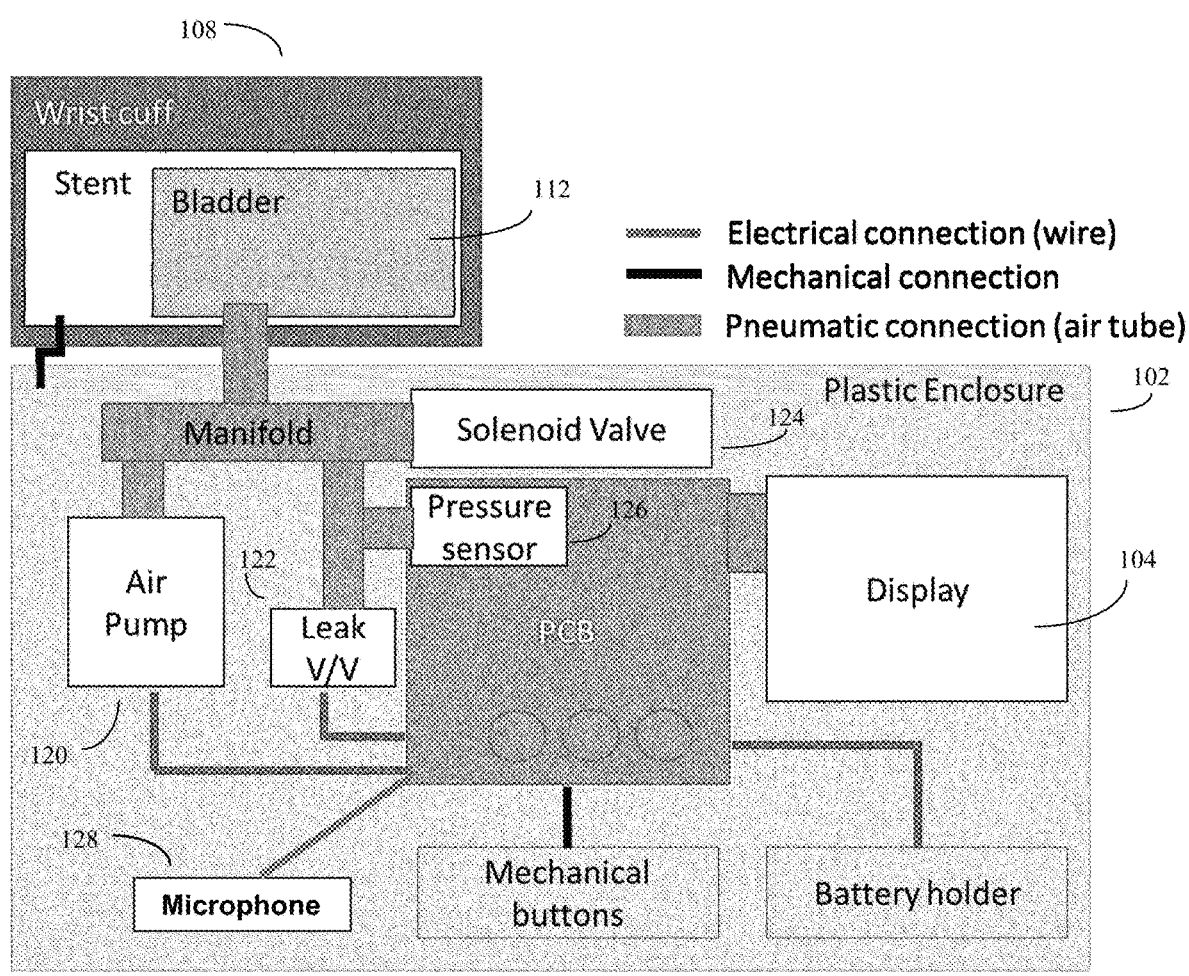
FIG. 2 shows a high-level mechanical architecture drawing of the device.

FIG. 2 shows a high-level mechanical architecture drawing of the device. The device's built-in microprocessor (200) (shown in FIG. 3 as µP), here built into the device's printed circuit board (PCB), receives input from the mechanical buttons and the pressure sensor and controls the operation of the air pump (120) and the solenoid valve (124), and optionally the leak valve (122). (In some embodiments, the leak valve (122) may be a passive leak valve). The device inflates and releases air pressure to and from the device's wrist-cuff air bladder (112) during operation. The air bladder pressure, which fluctuates both according to the inflation status of the bladder, and also in response to the user's pulse waves, is monitored by the pressure sensor (126). Thus, the measurements shown in FIGS. 5-6, 8, 12A, 14, 15-18 are obtained from the pressure sensor (126).

Figure 4:
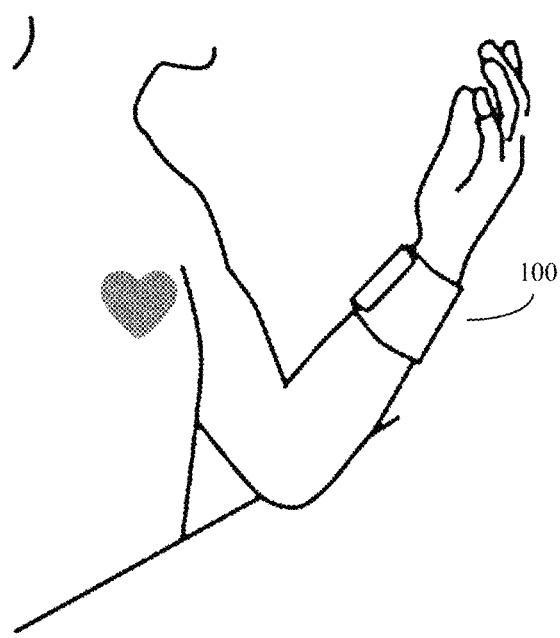
FIG. 4 shows how in in some embodiments, the device may be mounted on the user's wrist and elevated above a surface to approximately the level of the patient's heart.

An optional microphone (128), which in some embodiments may be used to detect audible breathing interruptions such as coughs or sneezing, or other audible breathing problems such as wheezing, is also shown. Note that this is a non-chest-contact microphone, which in some embodiments may be worn on the user's wrist as shown in FIG. 1 and FIG. 4. In alternative embodiments, the optional microphone may be part of a smartphone (240).

In some embodiments, if the patient makes audible breathing sounds that can be detected by the non-chest-contact microphone, these audible breathing sounds can optionally be used to improve the accuracy of the oscillometric derived breathing measurements.

The device's microprocessor also transmits information to the device's display (104), and if the display screen is a touch-sensitive display screen, it can also receive user input from the display. These parts are often at least partially enclosed in the plastic enclosure (102) shown in FIG. 1.

Figure 3:
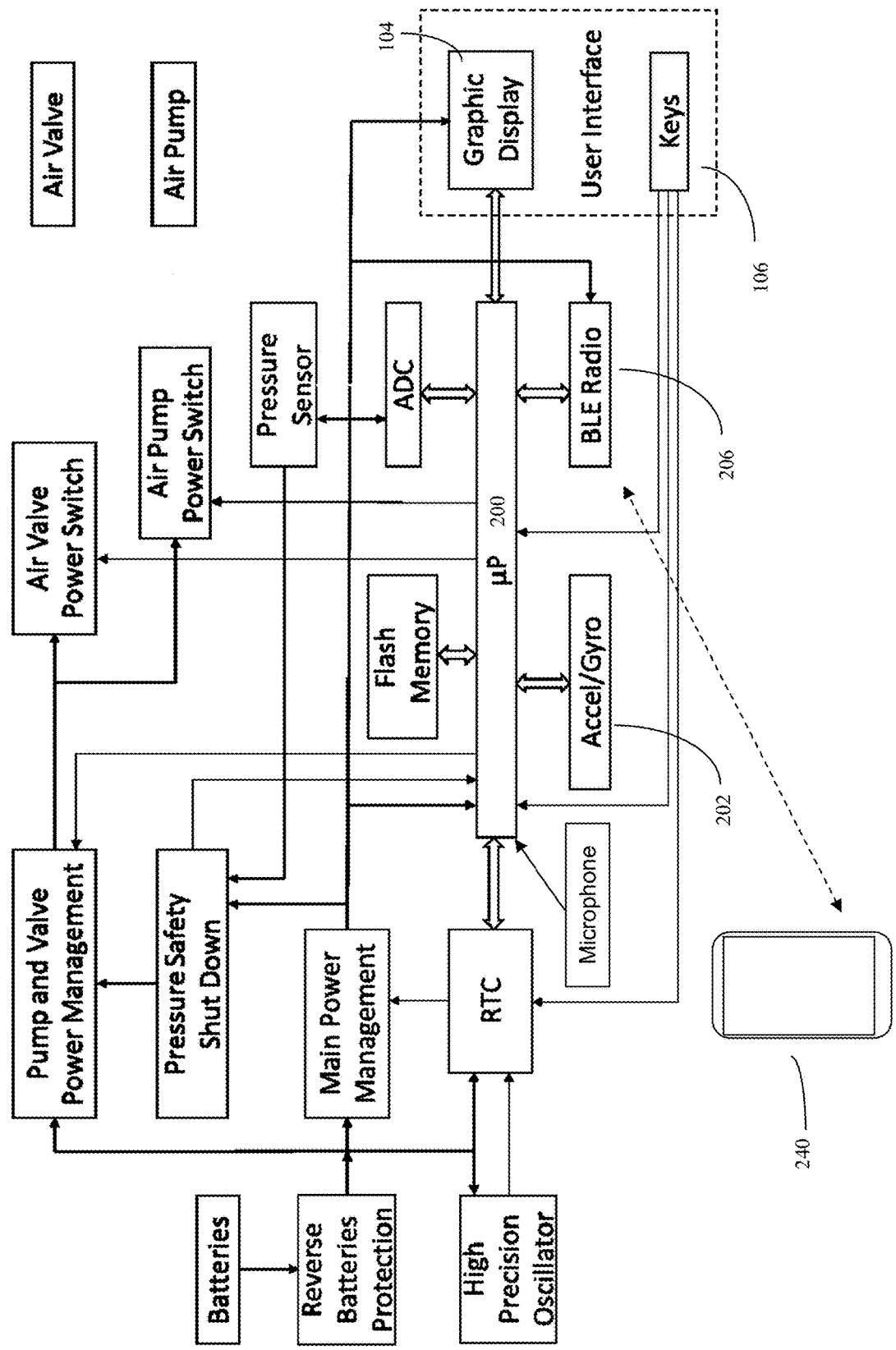
FIG. 3 shows the high-level electrical architecture of the device.

FIG. 3 shows the high-level electrical architecture of the FIG. 1 device. Note that although in this embodiment, the device has an accelerometer/gyroscope sensor, such as a Bosch BMI160 type accelerometer/gyroscope chip (202), which is a motion sensor (non-physiological sensor), this embodiment of the invention need not have other physiological sensors, such as pulse oximeters/PPG sensors and ECG sensors, which are sometimes used in other devices to help obtain breathing rate measurements. An optional microphone is also shown.

Figure 11:
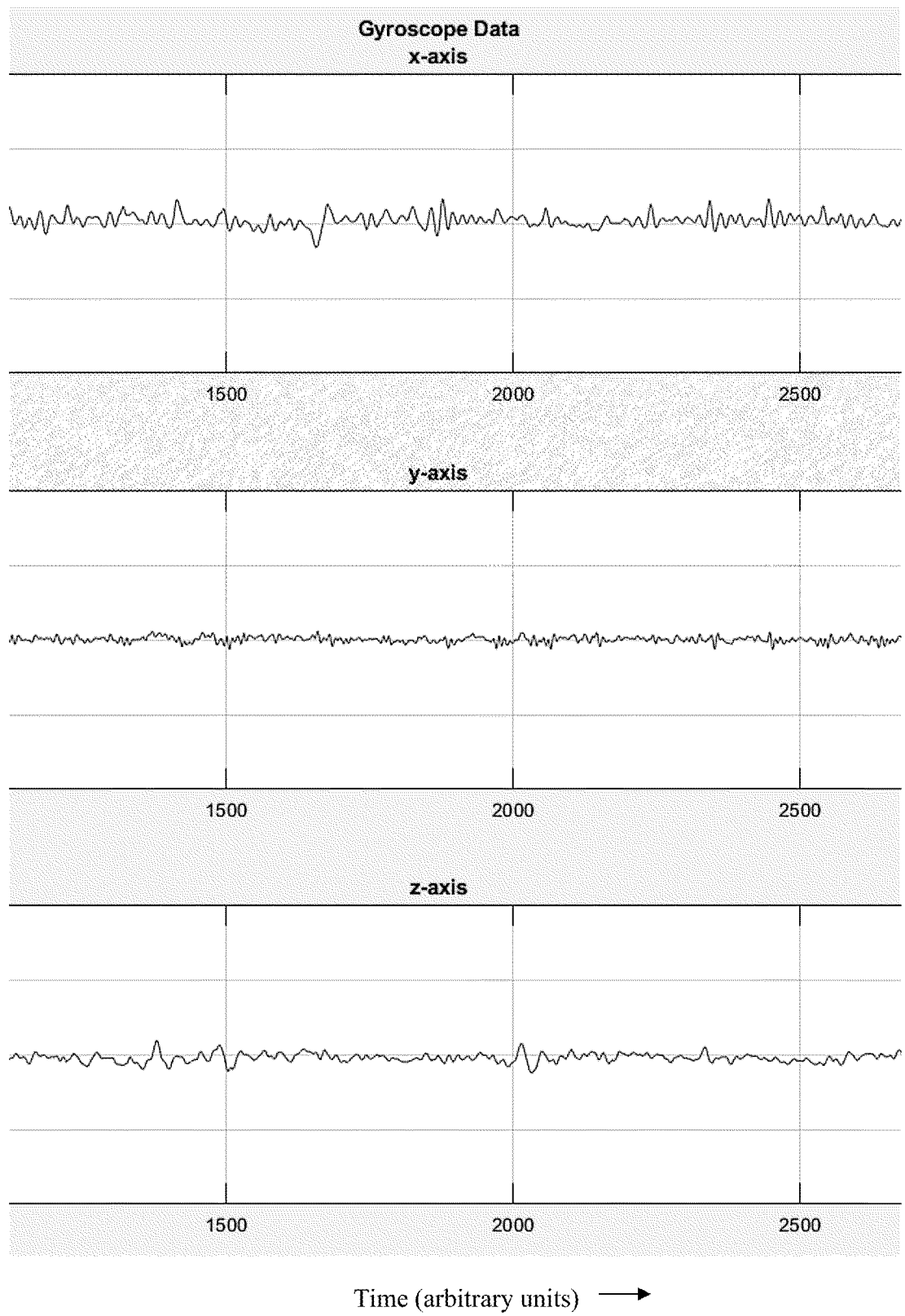
FIG. 11 shows the X, Y, and Z channels of the invention's optional accelerometer/gyroscope sensor showing relatively constant values when this sensor (and the corresponding device) is not moving.
Figure 12A:
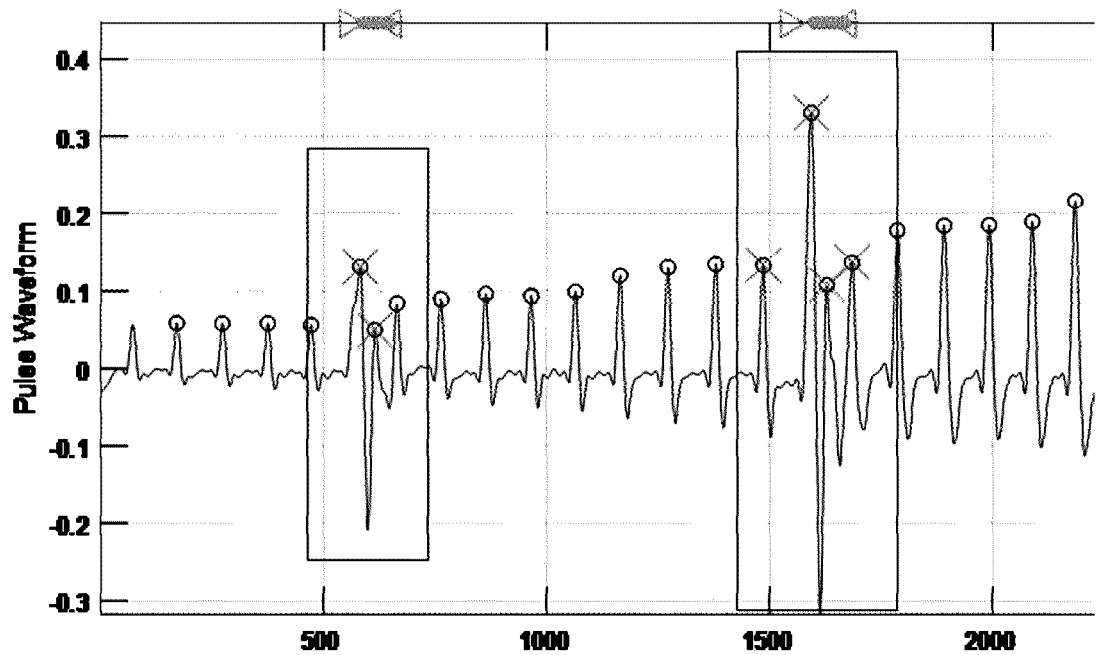
FIG. 12A shows the impact of user wrist movement on the wrist-mounted device during a reading. Such movement can produce pulse waveform artifacts (shown in the boxes).
Figure 12B:
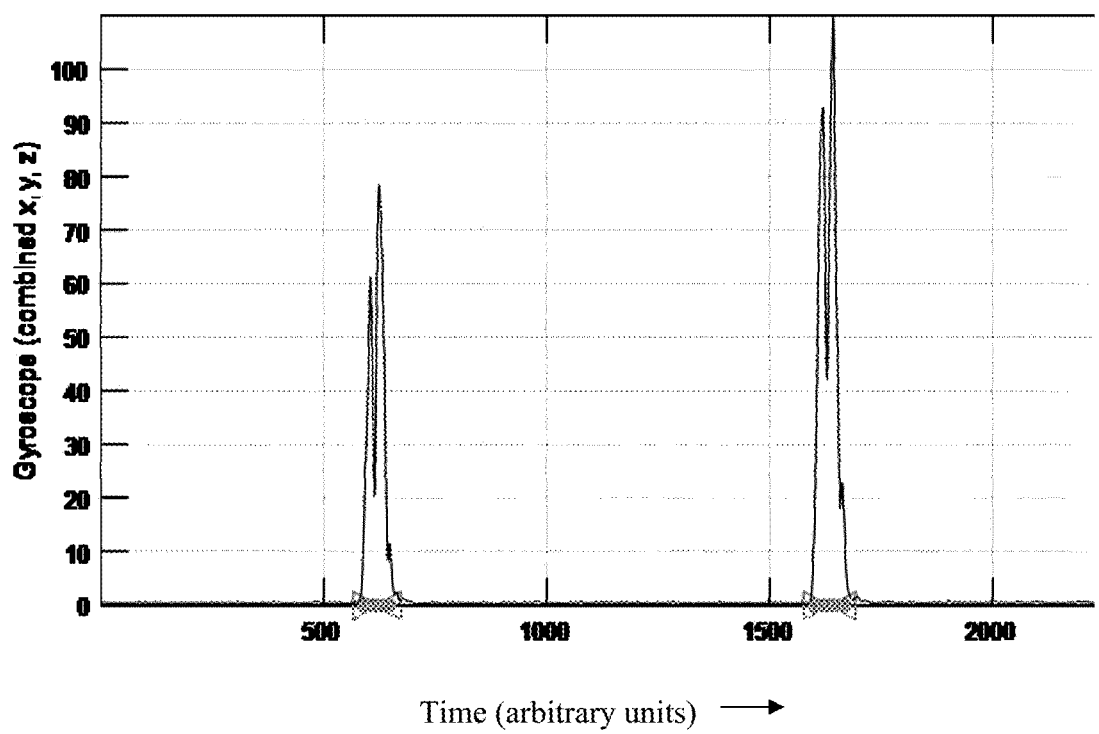
FIG. 12B, which shows the output from the device's optional accelerometer/gyroscope sensor during the same time as FIG. 12A, illustrates how the invention's accelerometer/gyroscope sensor can detect this movement and report the movement to the motion artifact detection algorithm shown in FIG. 13.

The measurements shown in FIGS. 11 and 12B were obtained from the accelerometer/gyroscope chip (202).

Put alternatively, in some embodiments, the device is an oscillometric device that comprises at least one processor (200). This device can optionally further include a display (104) configured to display the user's breathing rate. Alternatively, the device's optional wireless transceivers such as the Bluetooth transceiver (206) (BLE Radio shown in FIG. 3) can transmit this data to an external device such as a smartphone or other suitable wireless device (240).

FIG. 4 shows how in in some embodiments, the device (100) may be mounted on the user's wrist, with instructions to elevate the wrist above a surface to approximately the level of the patient's heart. The patient/user will typically be given instructions to not move their arm during the breathing rate measurement. Here the optional accelerometer/gyroscope sensor (202) is useful to verify that the patient is complying with these instructions. In general, the device may be mounted on a limb of a patient or user, such as the patient's or user's wrist.

One of the reasons why there is little or no prior art on using oscillometric devices to obtain breathing data (at least in the absence of supplementary pulse oximeter data or ECG data) is that the impact of breathing on the oscillometric data is relatively subtle, and is often hidden or obscured by various noise sources. Thus, the present invention relies, in part, on various novel and experimentally determined systems and methods to reduce the noise to the point where the weaker breathing signal can be obtained from the oscillometric data.

System and Algorithm Development

The development of the present invention's system and method relied on clinical testing, and experimentation with alternative devices and alternative algorithms.

As one example of such clinical testing, consider one test which was conducted at Dalhousie Medicine New Brunswick in Saint John, NB, Canada. One test involved a total of 27 healthy participants (6 male, 21 females; aged 22-55, mean±SD=36.6±9.1 years). Experiments were conducted under human ethics approval and written informed consent was obtained from each participant before enrollment.

Auscultatory breathing rate measurements were made by two trained observers using a dual stethoscope, while the device made simultaneous breathing rate measurements during the deflation of the wrist cuff. For each participant, a total of six readings were collected: three non-paced readings (participant breathing naturally) and three paced readings (participant breathing at: 8 breaths/minute, 16 breaths/minute, and 24 breaths/minute). This raw data was then used to evaluate various algorithms. Other experimental tests were also conducted.

As a result of such experimental testing, various aspects of the work were determined on somewhat of a trial-and-error basis. Certain aspects of the invention, discussed below that were implemented as a result of this trial-and-error clinical testing include:

Use of accelerometer/gyroscope sensor data for motion artifact detection
Removal of envelope outliers
Variable movement sensitivity based on arm position
Inclusion of a comparison check between "AM" breathing rate determinations and "FM" breathing rate determinations These experimentally determined systems and methods will be discussed in more detail in the following sections.

As previously discussed, in some embodiments, the invention may be a device, system, or method for automatically determining a breathing rate of a patient (or user). Expressing the invention in methods format, this method can comprise various steps. These steps can include obtaining pulse waveforms from an oscillometric device (100) mounted on a limb of the patient or user. These pulse waveforms are then analyzed, using at least one processor, and artifact-free regions of these pulse waveforms are automatically determined, thus obtaining edited (or alternatively weighted) pulse waveforms.

The at least one processor (200) will then automatically analyze these edited pulse waveforms. The AM envelope signals and FM between-pulse-time signals of these edited pulse waveforms are then determined. These AM envelope and FM between-pulse-time signals will be defined in more detail shortly. The processor(s) will further analyze these AM envelope signals and FM between-pulse-time signals and determine their AM envelope main harmonics and FM between-pulse-time main harmonics. Then, at least when these AM envelope main harmonics and FM between-pulse-time main harmonics are consistent, the processor(s) will calculate a weighted function of these AM envelope main harmonics and FM between-pulse-time main harmonics, and output (e.g., to a display screen 104, or transmit to another device 240) the result of this weighted function as the breathing rate of the patient/user.

As will be discussed in more detail, to ensure a reliable respiration rate result and a robust algorithm, in a preferred embodiment, automatically edited (artifact-free, or at least artifact reduced) regions of the pulse waveform are used. Regions corrupted by various artifacts (discussed shortly) are typically ignored.

For example, if the level of device movement is significant (too high) such that it will impact the accuracy of the algorithm to an unacceptable extent, the microprocessor (200) is configured to not return a respiration rate result. Instead, it is configured to output an error message.

If, on the other hand, some movement is detected, but the microprocessor determines that movement can be safely ignored, the device may return a respiration rate result, possibly along with a movement warning message, so that the user can be aware that the reported results may have somewhat suboptimal accuracy.

Although, not all versions of the device may comprise a display (104), in a preferred embodiment, the device may utilize a display, such as a thin film transistor (TFT) color display, to provide dynamic user feedback for movement and heart level warnings and errors as well as a real-time visualization of the pulse waveform during reading acquisition.

Experimentally, we have found that the sensitivity of the artifact detection is variable in that it depends on the user's arm position during the reading (see FIG. 4). This arm position can be determined by using the accelerometer/gyroscope sensor data (202) to calculate the forearm angle during a heart level determination algorithm. We have also found that if the user's forearm is raised at an angle, then the pulse waveform tends to be less prone to artifacts due to motion of the user's wrist since the wrist can move freely in the air.

However, if the user's forearm is rested flat on a surface, then the pulse waveform is generally more prone to artifacts due to the motion of the user's wrist since the user's wrist movement has a higher chance of encountering resistance from the surface. Thus, in some embodiments, the sensitivity of the artifact detection may be made variable (e.g., the accelerometer/gyroscope can determine this wrist angle, and vary the motion compensation algorithm accordingly) to accommodate this effect.

Thus, in some preferred embodiments, the oscillometric device will further comprise a tri-axial accelerometer/gyroscope device (202). This tri-axial accelerometer/gyroscope device will typically report the movement of the oscillometric device to the microprocessor(s) (200). The microprocessor(s) can then use this movement to determine motion artifact-free regions of the user's pulse waveforms for further analysis.

In general, pulse waveform artifacts (and the corresponding artifact-free regions of these waveforms) may be determined by any combination of various techniques, which will shortly be described in more detail. These techniques include using the cuff pressure signal to analyze the waveforms obtained during the cuff deflation (e.g., the deflation curve) by using the cuff pressure sensor (126) signal. Other techniques also include analysis of pulse cross-correlations using the cuff pressure signal, analysis of envelope outliers using the cuff pressure signal, and analysis of the tri-axial accelerometer/gyroscope signal.

More specifically, in some embodiments, the artifact-free regions of the pulse waveforms can be automatically determined by obtaining oscillometric cuff deflation signals, and analyzing these cuff deflation signals for areas where neighboring pulses exhibit below average cross-correlation. Alternatively, or additionally the device can use the tri-axial accelerometer/gyroscopic signals from the sensor (202) to automatically de-weigh (e.g., remove, or deemphasize) those cuff deflation signals obtained during the time in which the tri-axial accelerometer/gyroscope detects motion above a preset threshold. As yet another option, the invention may edit the envelope of the pulse waveforms, and automatically de-weigh (e.g., remove or deemphasize) the pulse waveform data associated with envelope outliers above a preset threshold.

Figure 5:
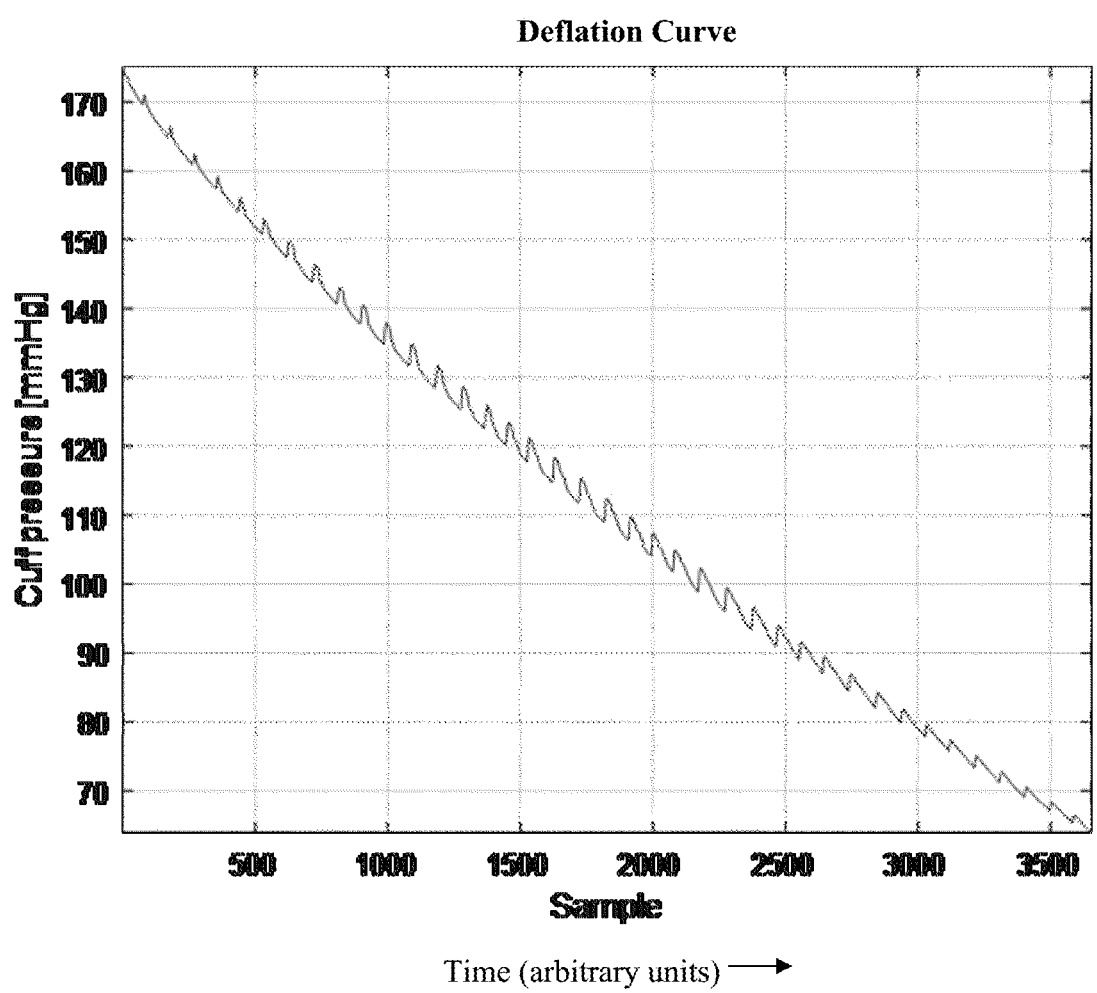
FIG. 5 shows an example of a cuff pressure signal waveform that can be obtained while the cuff deflates.

FIG. 5 shows an example of a cuff pressure signal waveform that can be obtained while the cuff deflates.

Figure 6:
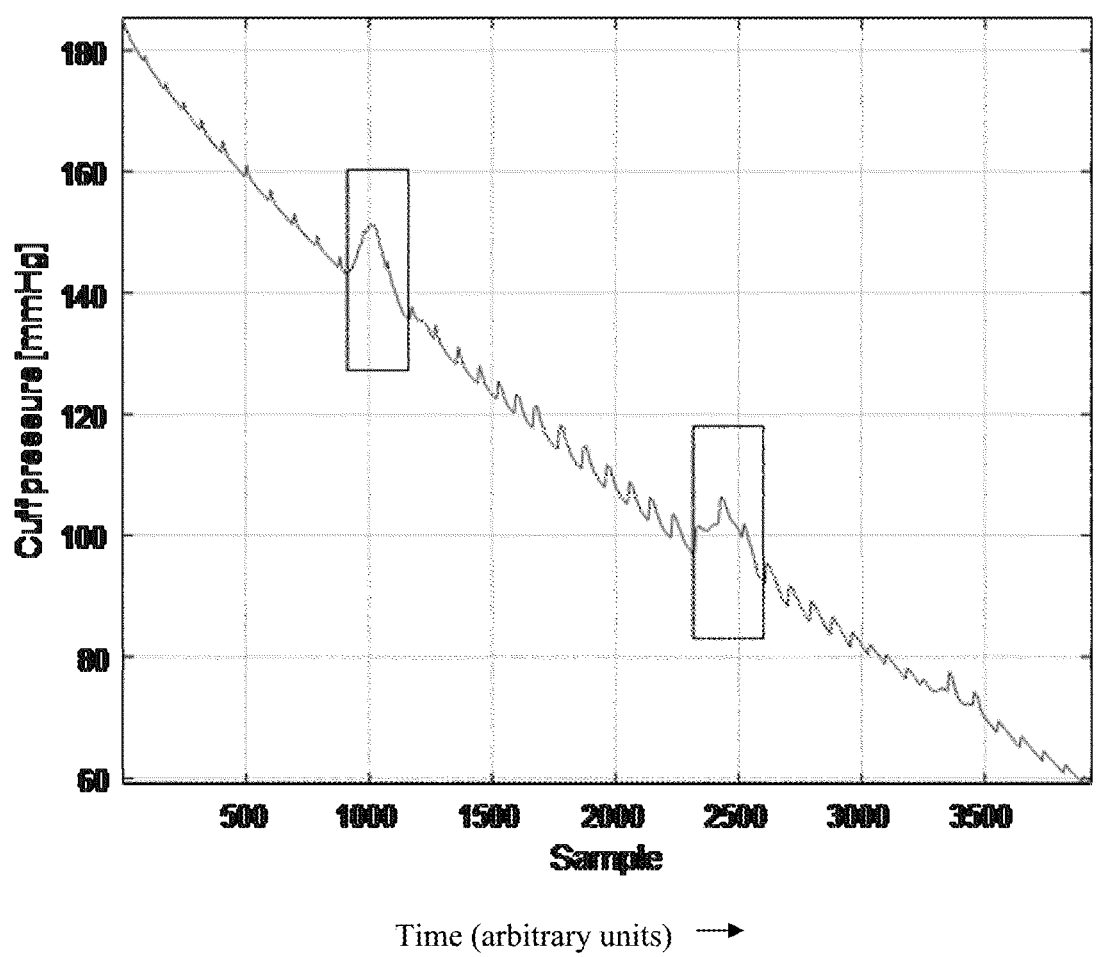
FIG. 6 shows an example of a cuff pressure signal obtained while the cuff is deflating. In this example, the signal also contains motion artifacts, shown in the two boxes.

FIG. 6 shows an example of a cuff pressure signal obtained while the cuff is deflating. In this example, the signal also contains motion artifacts, shown in the two boxes.

Figure 7:
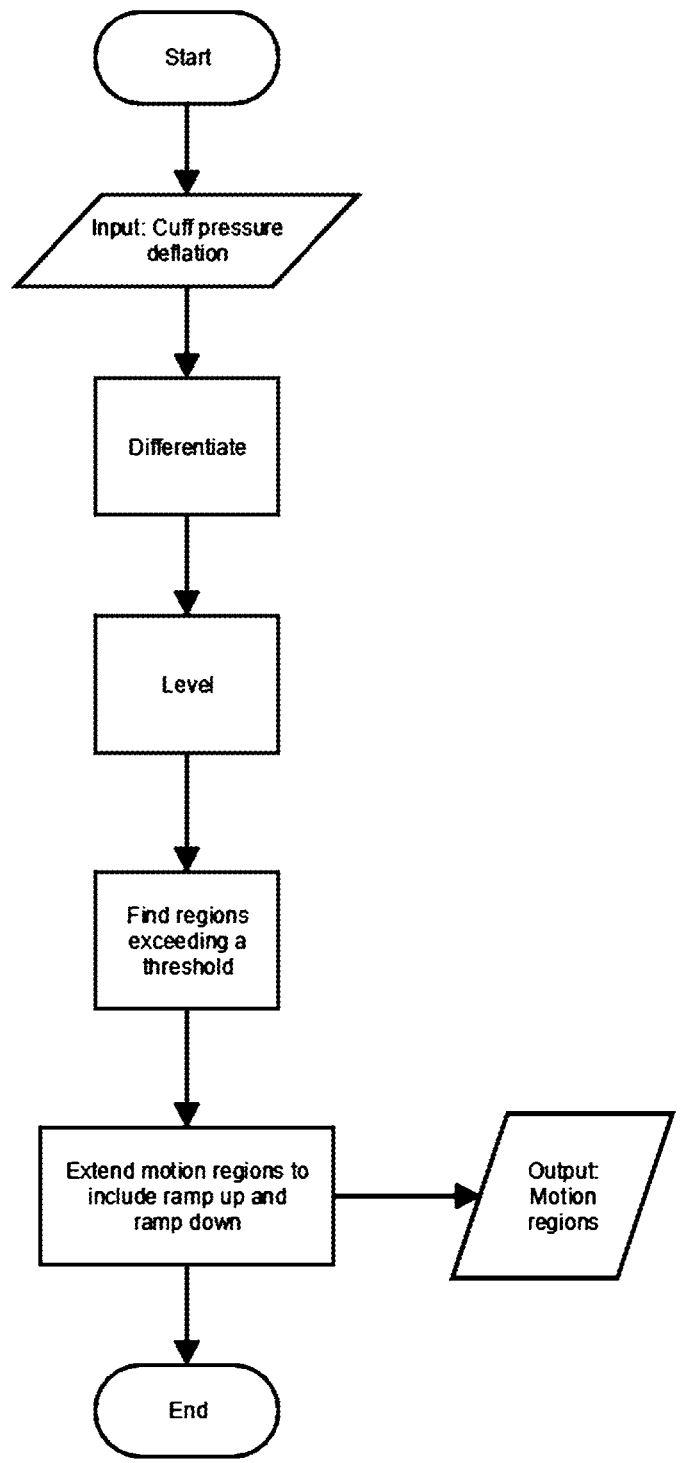
FIG. 7 shows a flowchart of one embodiment of the cuff pressure artifact detection algorithm.

FIG. 7 shows a flowchart of a cuff pressure artifact detection algorithm. Note that in the signal shown in FIG. 6, there is a high-frequency component, caused by the user's individual heartbeat pulses (e.g., one pulse per heartbeat). There is also a low-frequency component, caused by the gradual deflation of the device's cuff. (This gradual deflation is controlled by the device's processor 200, and the leak valve 122).

There are also intermediate frequency deviations, shown in the FIG. 6 boxes, where the cuff pressure data quickly rises above the expected low-frequency deflation curve threshold and then falls back. These can be determined by (in FIG. 7) configuring the processor (200) to differentiate the signal (optionally after a high pass filter to block the high-frequency component) and to look for regions (corresponding to the boxes in FIG. 6), where the rate of change exceeds an expected threshold. This allows the system to automatically "cut out" the suspicious data, and focus on the regions outside of boxes in FIG. 6. This is one type of edited pulse waveform data.

Determining other types of motion through analysis of the deflation curve using the cuff pressure signal: As shown in FIG. 5, the deflation curve is the waveform representing a decreasing cuff pressure signal. The user's pulse causes small deviations in the pressure, which is detected by the pressure sensor (126). These small pulse pressure "blips" (transient waveforms) contain blood pressure information. According to the invention, when outside noise is removed, these small blips also contain patient/user breathing rate information.

Unfortunately, the accelerometer/gyroscope signal cannot capture all types of hand motion artifacts. For example, the movement of the user's fingers may not always be captured by the accelerometer/gyroscope (202) because there is insufficient motion of the device (100) itself. However, we have found this type of patient/user finger movement can be detected because it creates predictable medium-scale artifacts in the deflation curve (see FIG. 6).

To detect this type of patient/user type of finger movement, shown in the boxes in FIG. 6, the processor can first use a lowpass filter to smooth the deflation curve and filter out (remove) the higher frequency radial pulse component of the signal. The lower frequency, but large amplitude, finger motion artifacts are unlikely to be removed by this low frequency filter. These finger motion artifacts can be detected as artifacts in the smoothed deflation curve. The finger motion artifacts, for example, will show up in the derivative of the smooth deflation curve. That is, the derivative of the overall deflation curve is nearly a constant, while the finger motion artifacts show up as changes in this derivative, and these can be automatically detected by the device's microprocessor. The microprocessor then knows to edit out these pulses, or at least deweigh those pulses in the boxed regions because they are at risk of having been distorted by finger motion.

A flowchart of this type of cuff pressure artifact detection algorithm is shown in FIG. 7.

Detection of "subtle" artifacts by analysis of pulse cross-correlations using the cuff pressure signal: Unfortunately, some types of remaining artifacts are too subtle to be detected by either the accelerometer/gyroscope signal or by using the deflation curve to detect additional types of motion.

Figure 8:
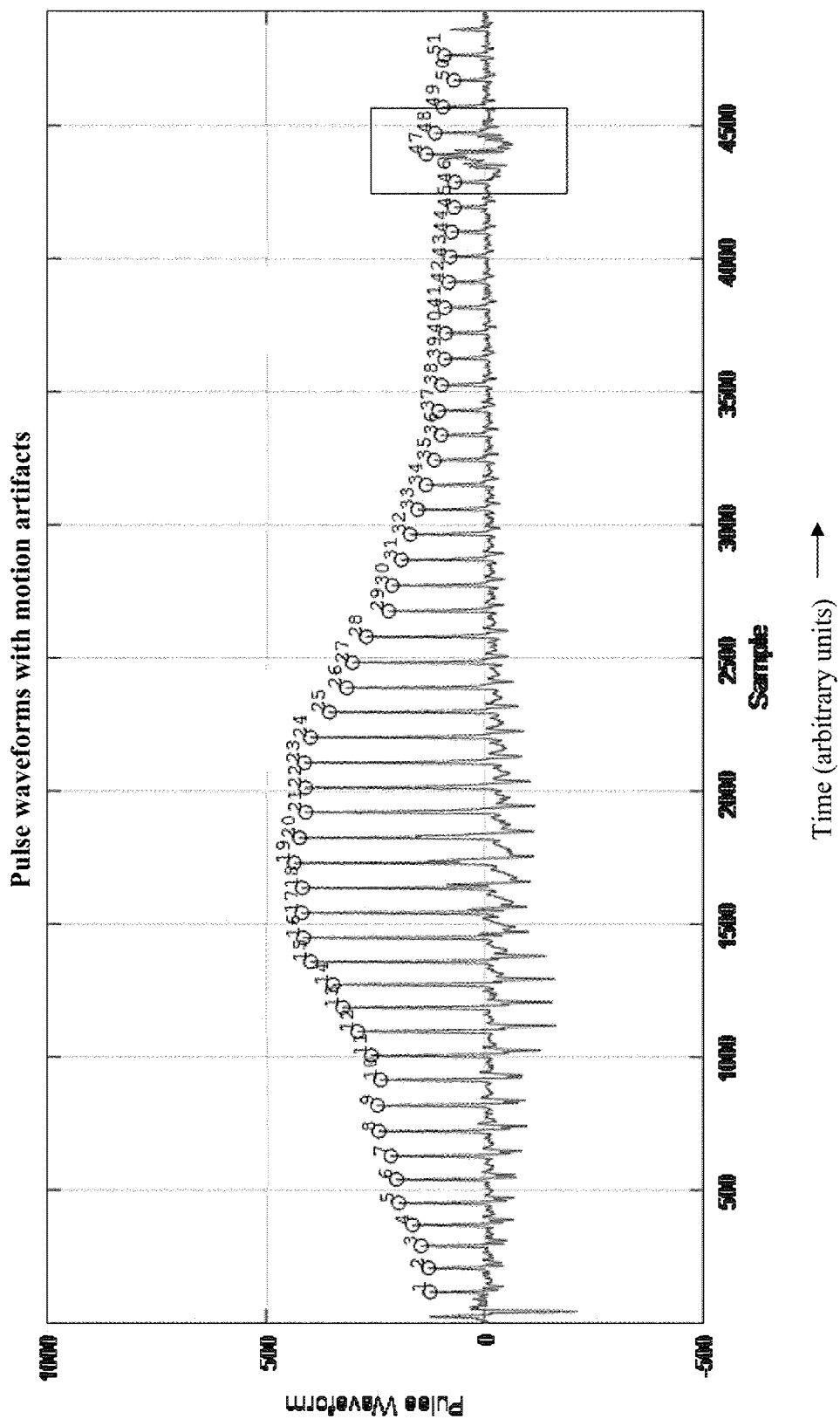
FIG. 8 shows an example of a pulse waveform. In this example, both pulse 46 and pulse 47 (shown in the box) contain motion artifacts. These can occur when the user moves their hand (see FIG. 4) during the breathing rate assessment.

As shown in FIG. 8, however, these "subtle" or "residual" artifacts may still corrupt the pulse waveform. To find these "subtle" or "residual" artifacts, the invention can use another technique that operates by determining the amount of cross-correlation between individual pulses. Through experimental work, we have found that both pulses with motion artifacts, and other types of "subtle" problems as well, exhibit a low correlation to other pulses throughout the waveform. This is shown in FIG. 9.

Figure 9:
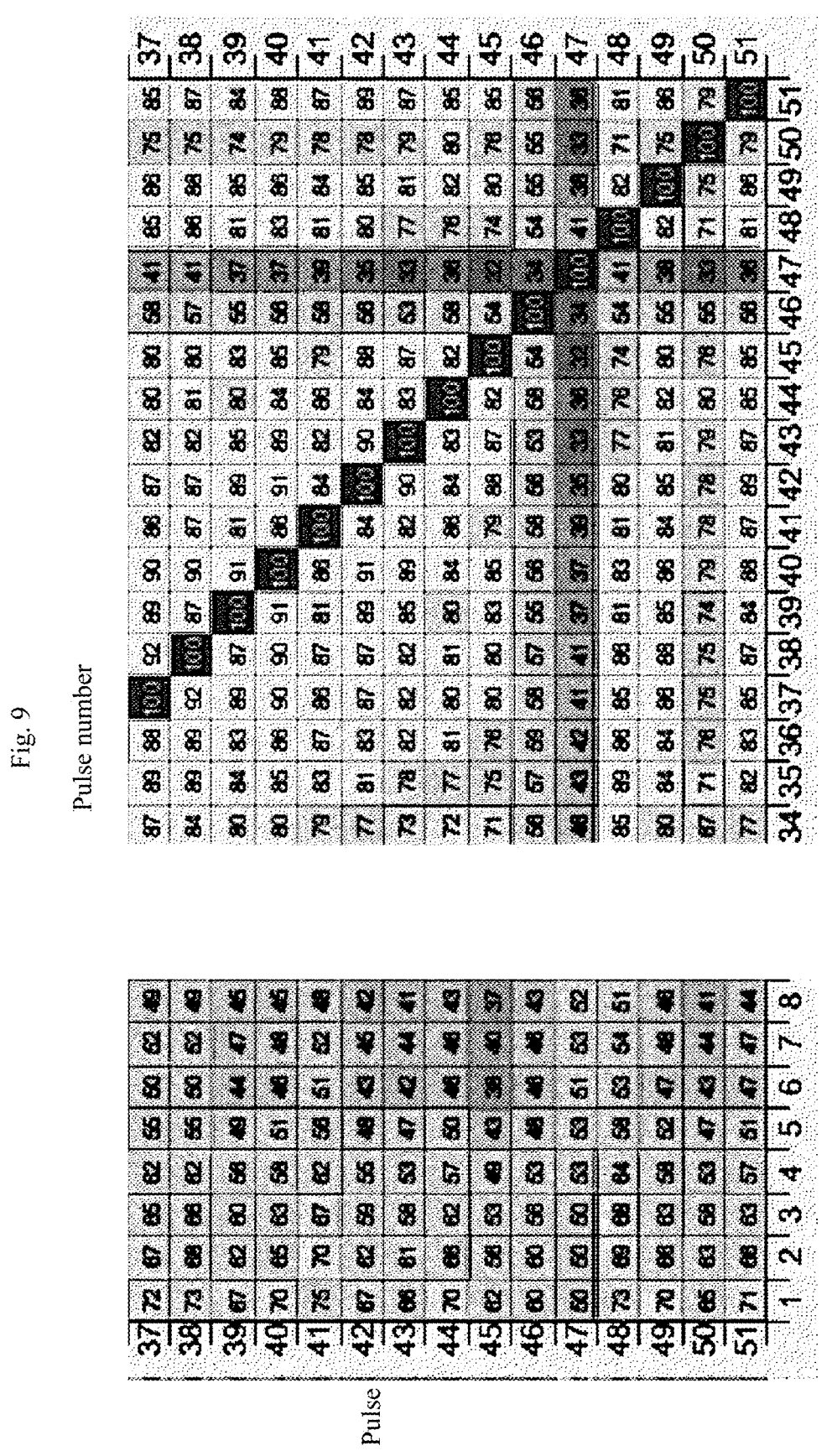

FIG. 9 shows an example of the data used by the invention's pulse percent residual difference (PRD) motion artifact detection algorithm. The numbers within the matrix are the modified PRD values that are calculated and which indicate the cross-correlation between pulses. In this example, the algorithm is detecting that individual pulses 46 and 47 previously shown in FIG. 8, show low correlation with their neighboring pulses. Here the percent correlation between neighboring pulses is shown in numbers, and significant differences are also shown in contrasting shades, forming a "cross pattern" centered on the intersection of pulse 47 with itself. Note that although an individual pulse will correlate 100% with itself, it will usually also correlate about 80-90% with its neighboring pulses. By contrast, Pulse 47 only correlates in the 30-40% range with its neighbors, and pulse 46 only correlates in the 50% range with its immediate neighbor pulses.

Here, according to the invention, the processor(s) computes these correlations using a modified percent residual difference (PRD) formula. This modified PRD formula enables a more sensitive measure of comparison than the more conventional Pearson correlation coefficient. A flowchart showing one embodiment of the invention's pulse PRD based artifact detection algorithm is shown in FIG. 10.

Figure 10:
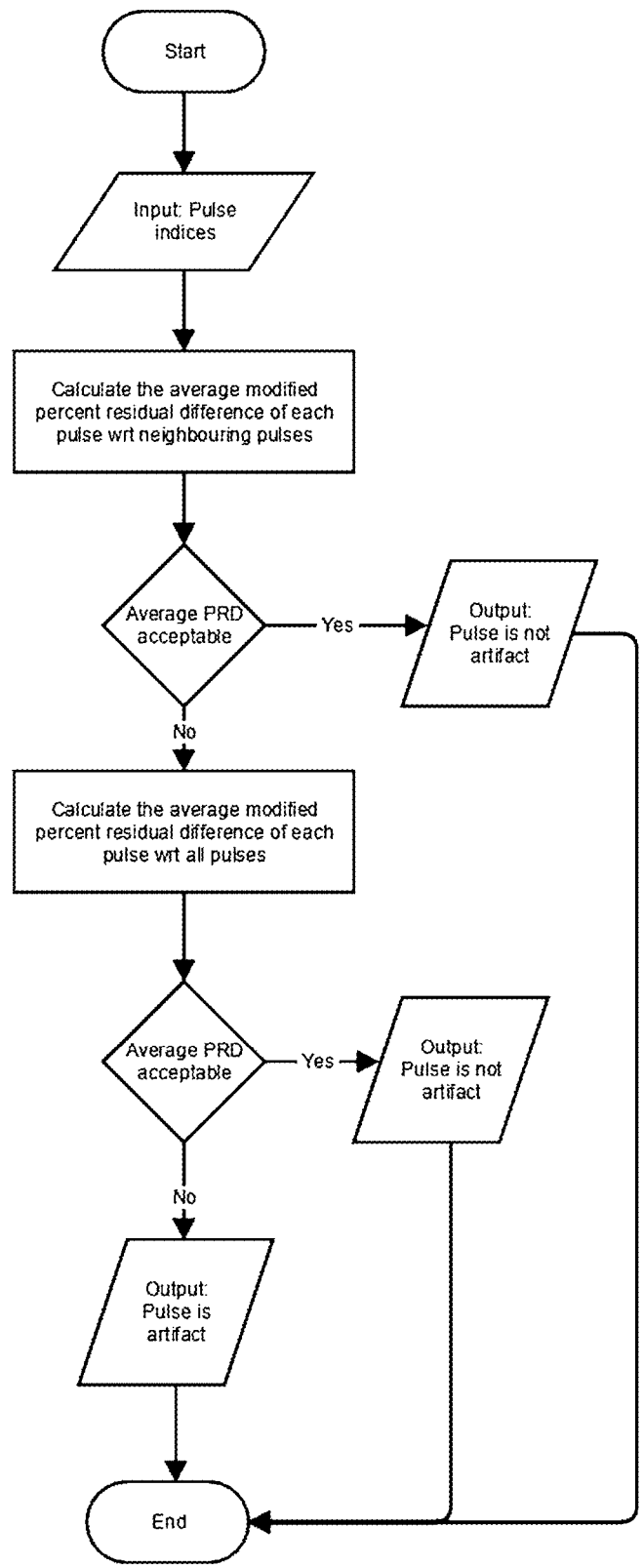
FIG. 10 shows a flowchart of the invention's pulse percent residual difference (PRD) motion artifact detection algorithm, which operated on the data previously shown in FIG. 8 and FIG. 9.

FIG. 10 shows a flowchart of the invention's modified pulse percent residual difference (PRD) motion artifact detection algorithm, which operates on the data previously shown in FIG. 8 and FIG. 9. Note that if the modified percent residual difference (PRD) is too high (see FIG. 8 and FIG. 9), this algorithm will determine that the output pulse is likely an artifact, and will thus either exclude this data and/or generate an error message.

Regarding analysis of the tri-axial accelerometer/gyroscope signal: In a preferred embodiment, the device's optional accelerometer/gyroscope sensor (here a Bosch BMI160) provides three channels of motion (accelerometer) data and three channels of gyroscopic data) representing motion in and around the x, y, and z axes. Generally, either a three-axis accelerometer or a three-axis gyroscopic sensor can work. When there is no movement of the device (100) during a reading, these data are relatively passive, i.e., low amplitude and flat. This is shown in FIG. 11. FIG. 11 shows the X, Y, and Z channels of the gyroscope sensor showing relatively constant values when the sensor is not moving. Note that the accelerometer/gyroscope sensor does not report data on the patient's physiological state.

According to the invention, at least some types of patient/user wrist movement during a breathing rate reading can be detected through the accelerometer/gyroscope data. This is shown in FIG. 12A and FIG. 12B.

FIG. 12A shows the impact of user wrist movement on the wrist-mounted device during a reading. Such movement can produce pulse waveform artifacts (shown in the boxes). FIG. 12B, which shows the output from the device's optional accelerometer/gyroscope sensor during the same time as FIG. 12A, shows how the invention's accelerometer/gyroscope sensor can detect this movement and report the movement to the motion artifact detection algorithm shown in FIG. 13.

Figure 13:
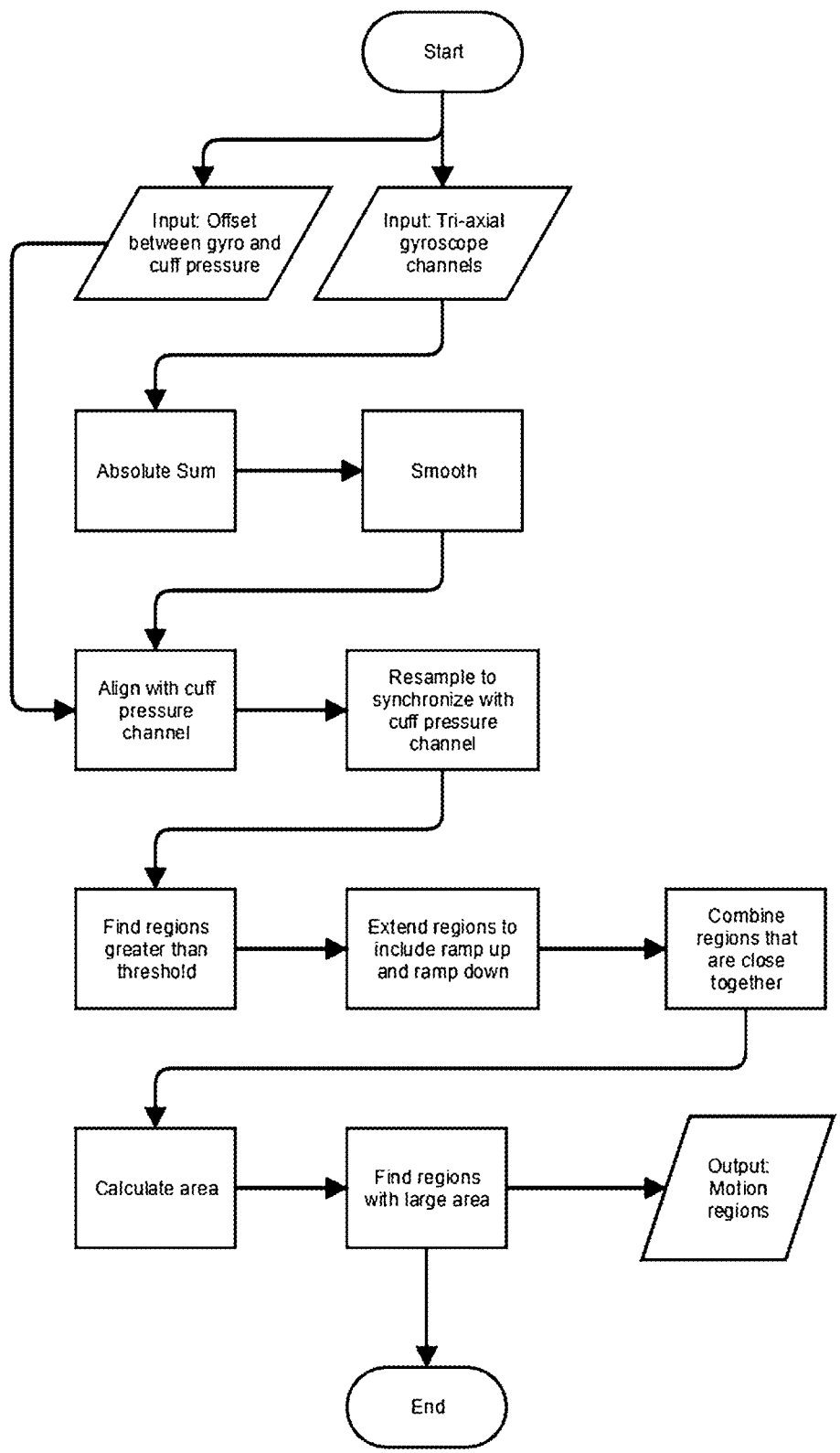
FIG. 13 shows a flowchart of the invention's accelerometer/gyroscope motion artifact detection algorithm.

FIG. 13 shows a flowchart of the invention's accelerometer/gyroscope motion artifact detection algorithm. This algorithm can take input from the oscillometric detector (FIG. 12A) and the accelerometer/gyroscope sensor (FIG. 12B) and output the motion free regions of the signal where good data can be obtained.

Figure 14:
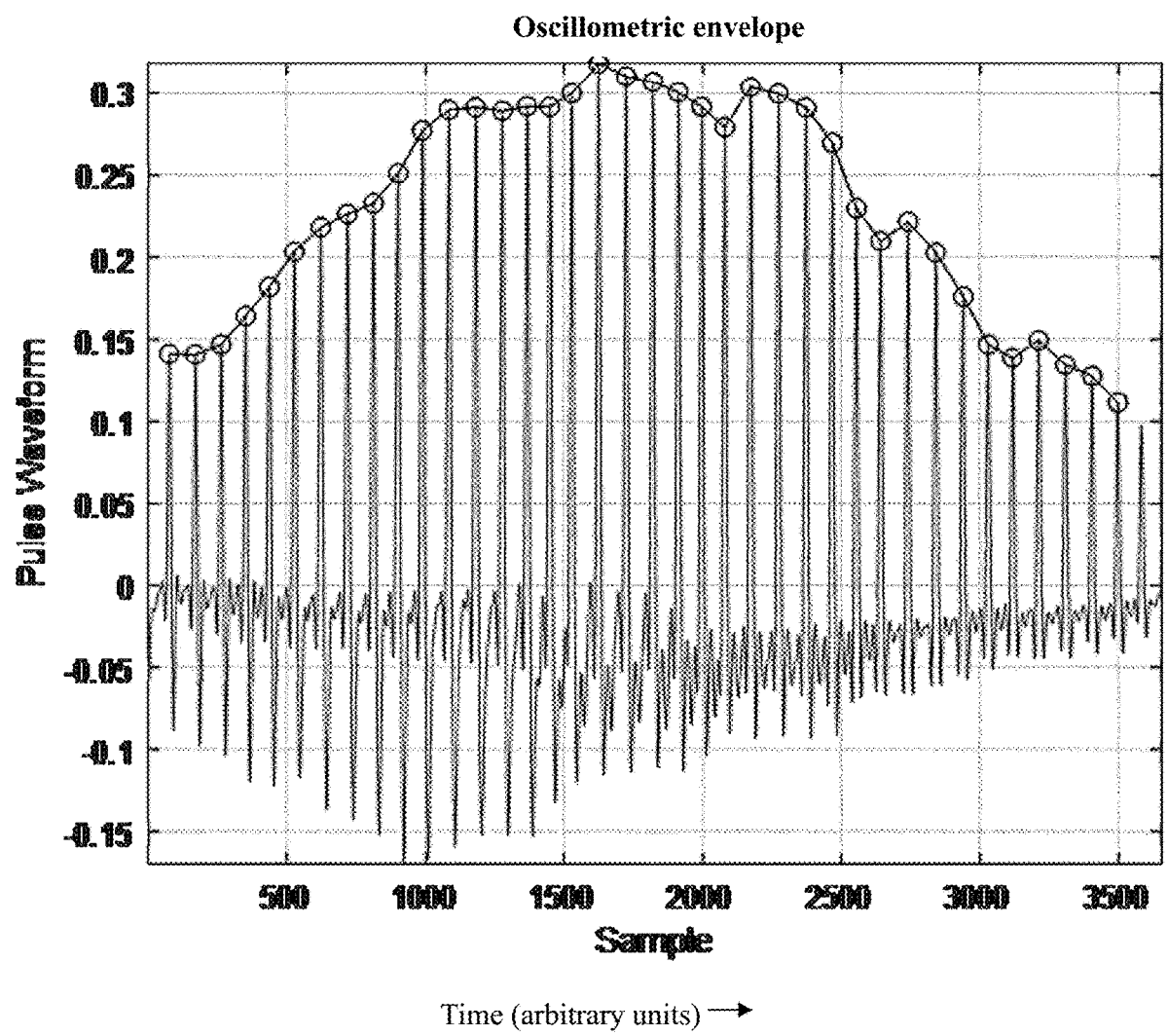
FIG. 14 shows how the user's pulse waveforms fit within an oscillometric envelope.

Other error detection algorithms—analysis of envelope outliers using the cuff pressure signal: Other algorithms may also be used to detect certain types of errors. For example, as shown in FIG. 14, the envelope of the pulse waveform exhibits a gradual rise and fall as the cuff pressure deflates from above the systolic blood pressure to below the diastolic blood pressure. However, certain pulses may not follow this expected behavior. Some pulses, for example, may instead exhibit a higher or lower than expected amplitude. In some embodiments of the invention, these "envelope outliers" can also be automatically detected and removed in order to prevent these envelope outliers from impacting the overall shape of the envelope.

FIG. 14 shows how the user's pulse waveforms fit within an oscillometric envelope. Notice the gradual rise and fall of the envelope. In some embodiments of the invention, to further reduce artifacts, individual pulses that do not adhere to this gradual slope can also be excluded by an appropriate error detection algorithm.

Thus, the invention uses multiple and redundant error detection methods to remove artifacts from the pulse wave signal. Due to this redundancy, although use of accelerometer/gyroscope sensor data to assist in error analysis is preferred, the system can also operate without use of the accelerometer/gyroscope sensor.

"AM" and "FM" Analysis Methods:

As previously discussed, according to the invention, in at least some embodiments, the processor(s) determines the previously discussed "AM envelope signals" and "FM between-pulse-time signals" by determining an oscillometric envelope of pulse peak amplitudes and times between individual pulses of the pulse waveforms. Here, we will discuss these techniques in more detail.

According to the invention, the "AM" signal is based on pulse peak amplitudes, that is, the oscillometric envelope of the pulse waveform.

By contrast, the "FM" signal is the instantaneous pulse rate signal (pulse rate per pulse), which is based on the timing of the individual pulse positions with respect to each other. These signals are extracted from the identification of pulses in the processed cuff pressure signal.

AM methods: Note that the envelope of the pulse waveform exhibits a gradual rise and fall as the cuff pressure deflates from above the systolic blood pressure to below the diastolic blood pressure (see FIG. 8). This is referred to as an oscillometric envelope. As the user breathes, the change in chest volume caused by air entering and exiting the lungs impacts the amplitude of the pulse acquired by the device. This mechanical influence of breathing causes a rise and fall in the pulse amplitude and is modulated within the oscillometric envelope. This is referred to as the amplitude modulation (AM) breathing signal (see FIG. 15). This name was chosen because the underlying method is somewhat analogous to AM radio in that information (i.e., breathing) is stored in the form of amplitude changes.

FM methods: As the user breathes, a natural phenomenon known as respiratory sinus arrhythmia impacts the pulse duration (e.g., time between neighboring pulses). This electrical influence of breathing causes an increase and decrease in the pulse frequency. This doesn't necessarily impact the amplitude of the oscillometric envelope, but does impact the time between successive pulse waves within the oscillometric envelope. This different effect has been named the "frequency modulation (FM)" breathing signal (see FIG. 16). It was given this name because this effect is somewhat analogous to FM radio. That is, here, the breathing rate information is stored in the form of frequency changes (e.g., times between successive pulse waves).

Figure 15:
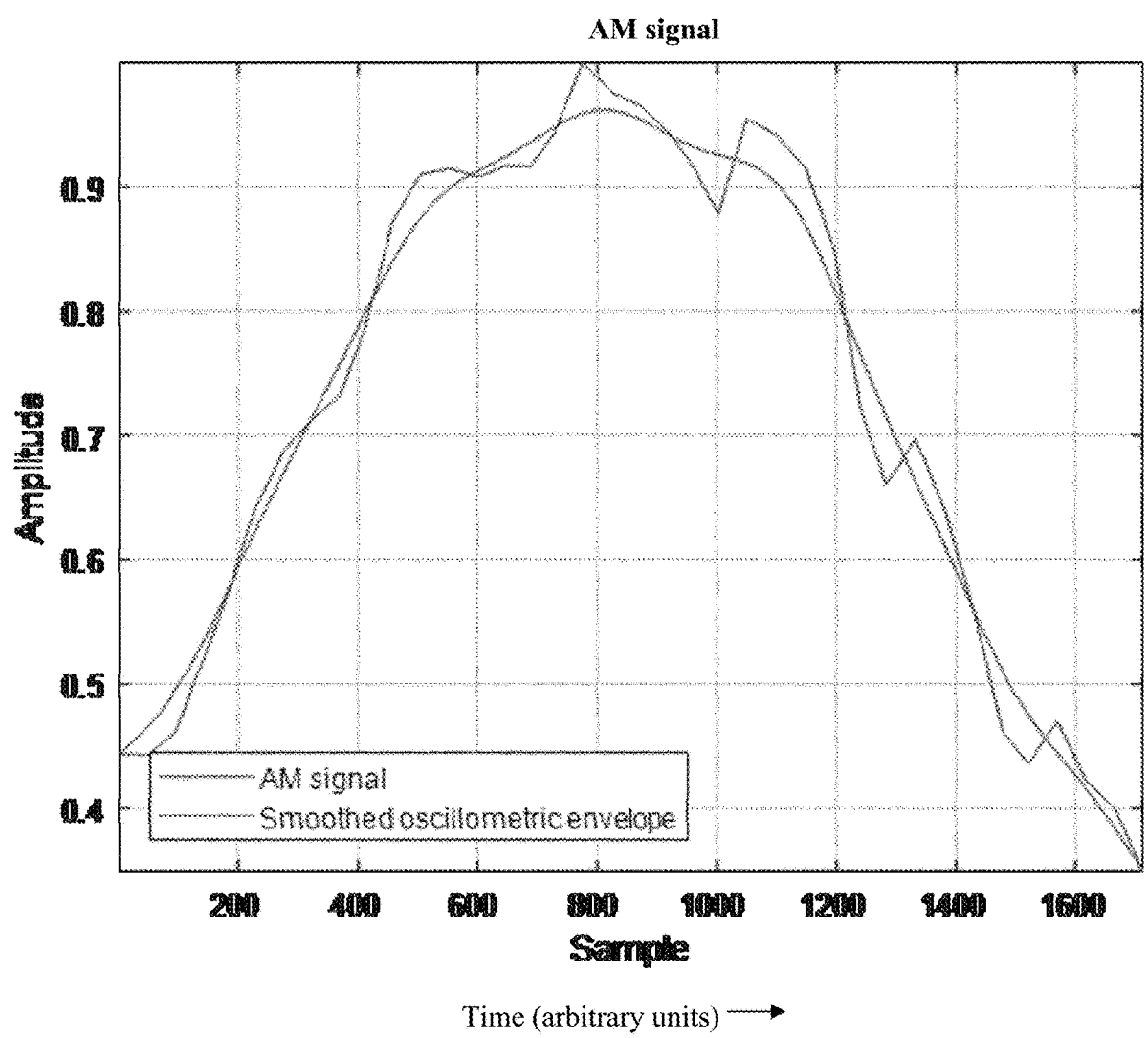
FIG. 15 shows the invention's "amplitude modulation" (AM) type breathing signals.

FIG. 15 shows the invention's "amplitude modulation" (AM) type breathing signals. In this figure, the invention's AM signal both rises above and falls below the smoothed oscillometric envelope. This rise and fall of amplitudes (e.g., deviation from the smoothed envelope) is caused by the mechanical influence of the user's chest motions during breathing. This is, in essence, one type of "breathing rate" signal, which can often be obscured unless at least some of the various previously described artifacts are removed.

Figure 16:
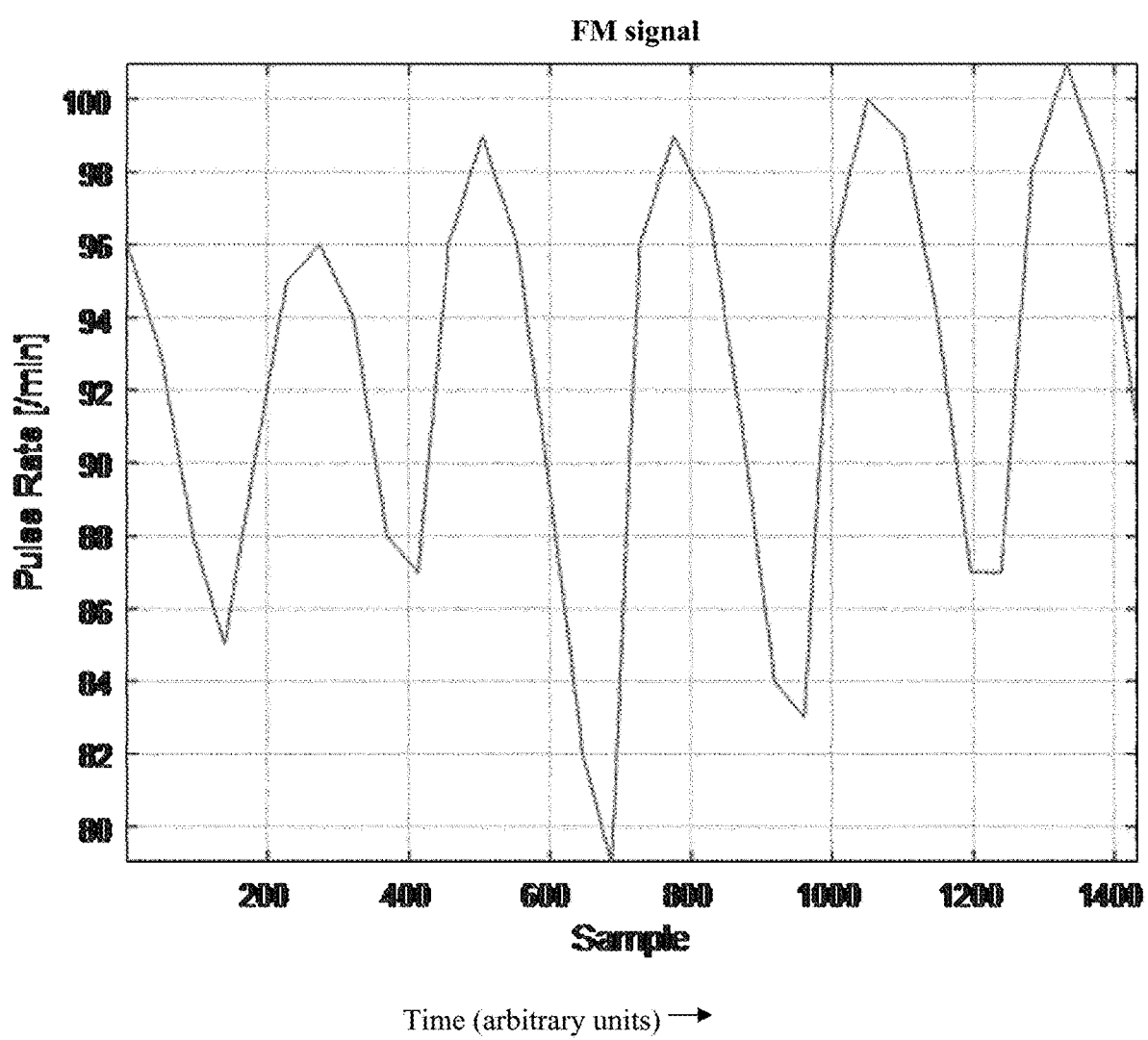
FIG. 16 shows an example of the invention's "frequency modulation" (FM) type breathing signal.

FIG. 16 shows an example of the invention's "frequency modulation" (FM) type breathing signal. The instantaneous pulse rate (e.g., time difference between successive pulses) rises and falls throughout the pulse waveform. This rise and fall of frequencies are associated with the electrical influence of breathing. In other words, during one phase of respiration, the pulses occur quicker together in time, while in a different phase of respiration, the different pulses occur slower in time. This is a second type of "breathing rate" signal that can often also be obscured unless at least some of the various previously described artifacts are removed.

Thus, in some embodiments, the processor(s) further determines the FM between-pulse-time signals by computing time differences between peak indices of the pulse waveforms and using these time differences to calculate instantaneous pulse rates of the patient/user. The processor can then use these instantaneous pulse rates to determine the FM between-pulse-time signals.

Further, in some embodiments, the processor determines the AM envelope main harmonics and FM between-pulse-time primary harmonics by computing a Fourier transform of the oscillometric envelope of the pulse waveform; and calculating a Fourier transform or power spectral density of the FM between-pulse-time signals (e.g., determine the primary/main harmonics by assessing an instantaneous pulse rate signal based on the pulse positions with respect to each other).

More specifically, the main harmonics of the AM and FM signals can be determined through frequency-domain analysis (such as, power spectral density). Here, the time-domain representations of the AM and FM signals are shown in FIG. 15, and FIG. 16, respectively.

According to the invention, the patient's or user's respiration rate can be derived from the main harmonic of each of these waveforms. The main harmonic, which is an indication of the highest-amplitude frequency, can be determined by converting the time-domain waveforms to their frequency-domain representations. This can be done by various methods, including the Fourier transform, using a power spectral density (PSD) estimate via Welch's method, and other methods. Once this is done, the processor then automatically determines the frequency with maximum power in the range of interest (e.g., within physiological breathing rate ranges).

Figure 17:
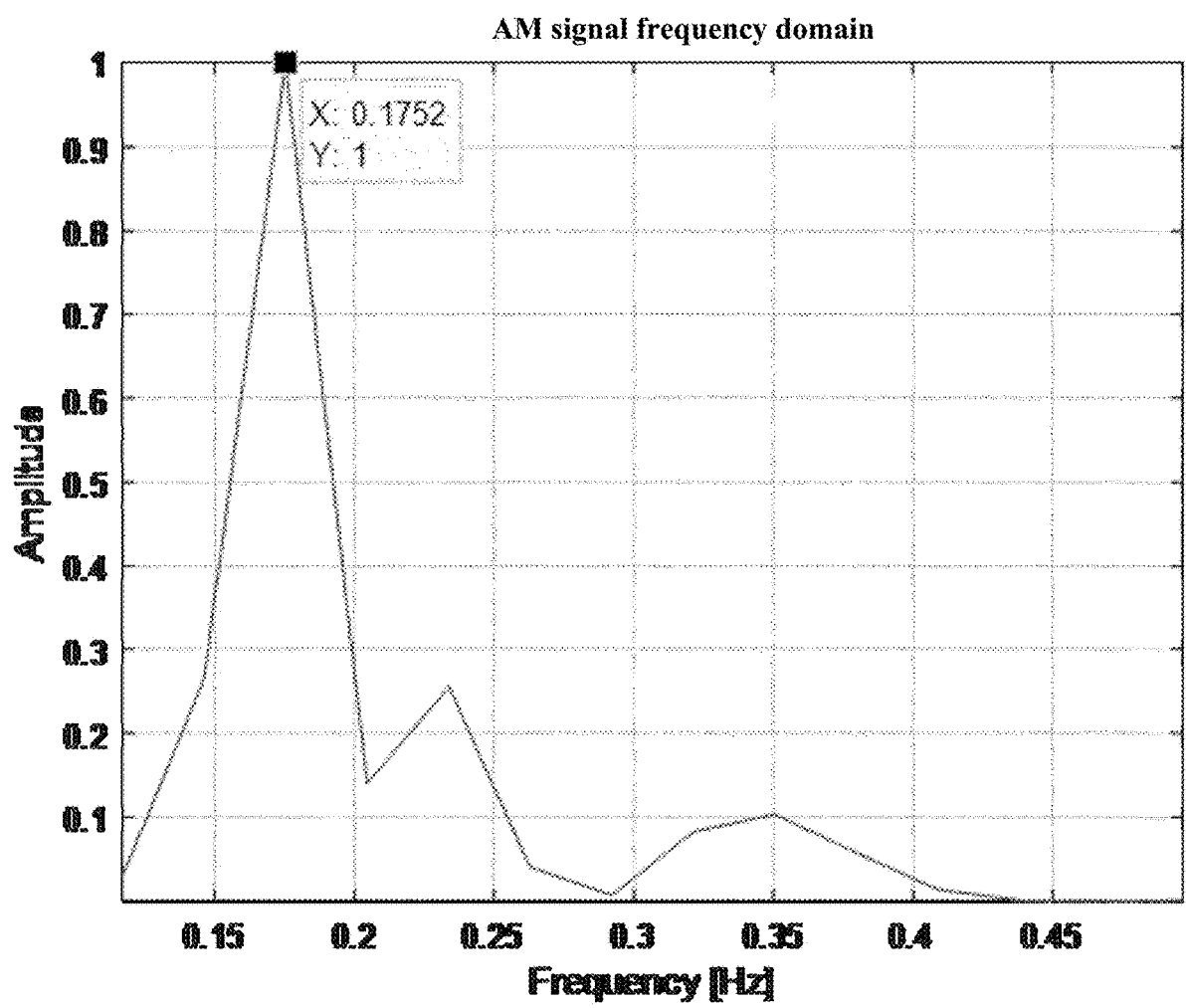
FIG. 17 shows a frequency-domain representation of the amplitude modulation (AM) breathing signal from FIG. 15.

FIG. 17 shows a frequency-domain representation of the amplitude modulation (AM) breathing signal from FIG. 15. The main harmonic can be seen as 0.1752 Hz, which is an AM signal calculated breathing rate of 10.51 breaths per minute.

Figure 18:
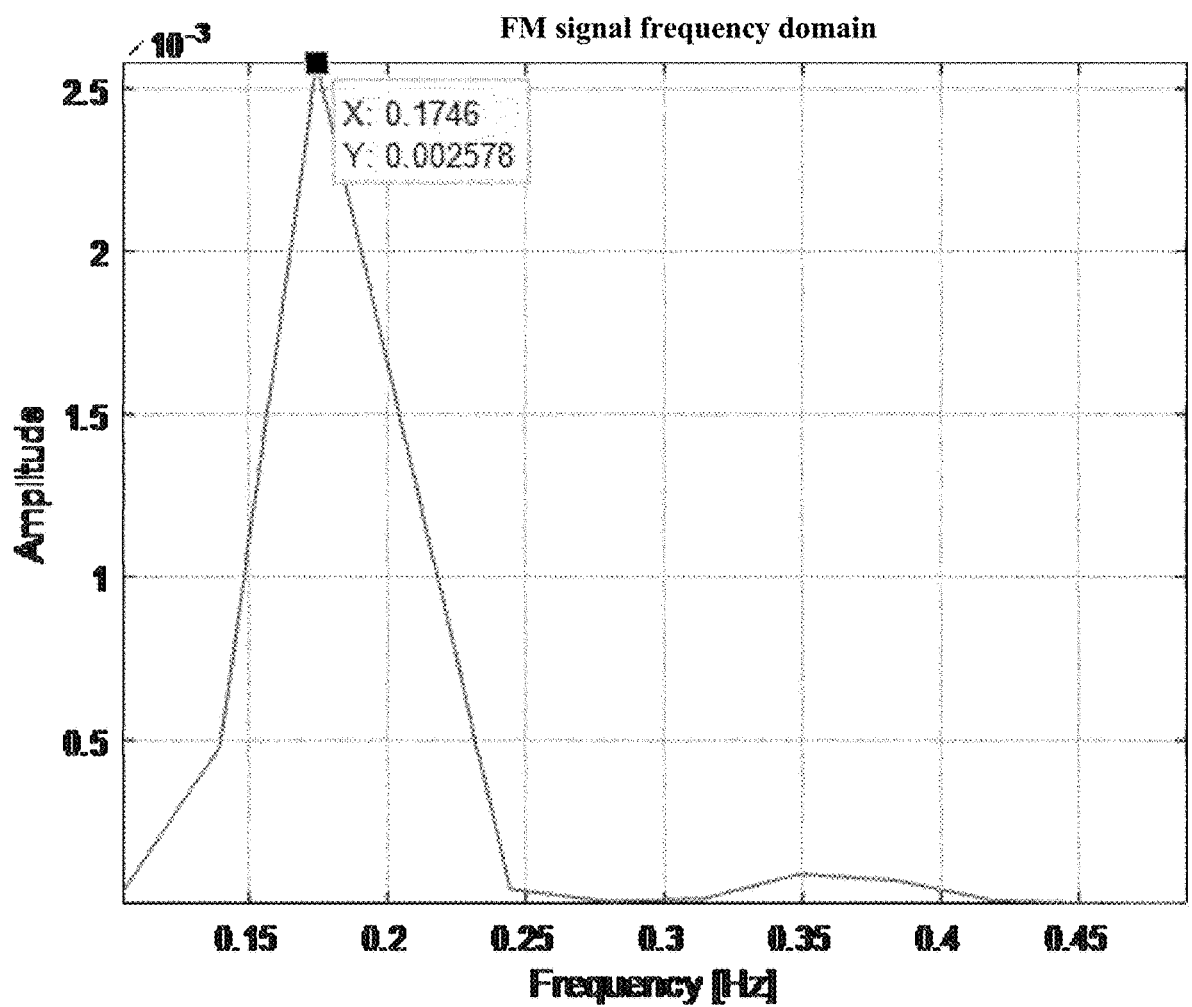
FIG. 18 shows a frequency-domain representation of the frequency modulation (FM) breathing signal from FIG. 16.

FIG. 18 shows a frequency-domain representation of the frequency modulation (FM) breathing signal from FIG. 16. The main harmonic can be seen as 0.1746 Hz, which is an FM signal calculated breathing rate of 10.48 breaths per minute.

Error Detection Methods Based on Comparing the AM Signal Vs the FM Signal:

In some embodiments, processor(s) can determine if the AM envelope main harmonics and FM between-pulse-time main harmonics are consistent with each other. To do so, the processor(s) can compare the AM envelope main harmonics with the FM between-pulse-time main harmonics, and check if these are close in value within a predetermined limit.

Here, for example, the invention can determine a respiration rate average based on both signals. That is, there is one respiration rate for the AM signal, and another for the FM signal. The agreement of these results provides confidence in the respiration rate average. A significant disagreement of these results indicates a potential error condition.

Based on experimental studies, we have found that the AM signal should be given a higher weight than the FM signal for optimal accuracy (versus a reference respiration rate). However, when the calculation of the respiration rate from the AM signal differs from that calculated from the FM signal by a specific ratio of the AM result, then the accuracy performance of the final result is likely to be lower than desired. This may be a possible error condition, or at least a caution indication. The processor can be configured to report warnings or errors depending on these results.

Based on experimental studies, we have further found that to improve confidence in the final breathing rate result, the processor should preferably make a comparison between the result coming from the AM signal against that coming from the FM signal. For example, this can be done by determining the respiratory rate average RRA, where:

$$|RRA_{AM} - RRA_{FM}| > r*RRA_{AM}.$$

In some embodiments, if this confidence check fails, then the processor is configured to return an error message rather than a breathing rate.

Further, in some embodiments, the final reported respiration rate may be determined to be a weighted combination of the AM result and the FM result.

For example, in some embodiments, the system may compute a weighted combination of the AM result and the FM result following the respiratory rate average (RRA) equation:

$$RRA = (a_1 * RRA_{AM}) + (a_2 * RRA_{FM}) + b.$$

Here, the weighting coefficients, $a_1$ and $a_2$, and offset, b, may be determined experimentally (e.g., through optimization of performance during algorithm calibration), and may then be stored in the device's memory for future use.

Graphical display for rapid breathing rate classification.

Once determined, the average breathing rate can further be classified for adults as low (for example, <12/min), normal (for example, 12-20/min) or high (for example, >20/min) based on generally accepted values. In some embodiments, such a classification may be displayed on the device screen to aid in interpretation of the result, with care not to confuse this with diagnosis of respiratory conditions. With the aid of a graphical display, such as a color graphical display, this can be further elaborated to include visual indicia, such as colors to represent the classification including the use of a visual gauge to indicate the relative position with respect to the classification regions. This type of graphical output (here down-converted to black and white for the purposes of this patent figure) is shown in FIG. 19.

Figure 19:
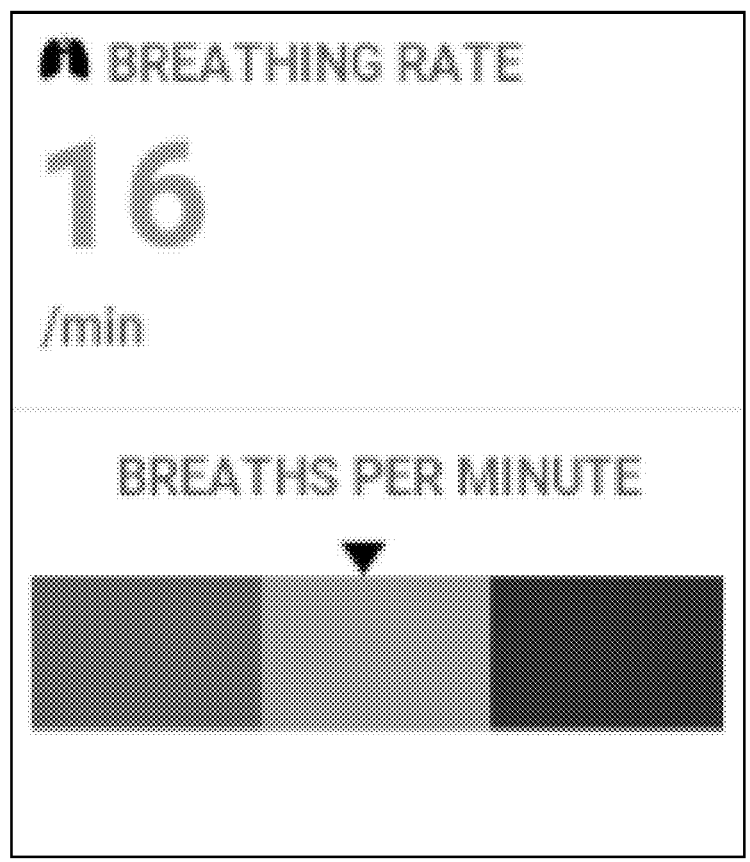
FIG. 19 shows an example of a graphical output of the breathing rate. Here, in the original form, the colors ranged from blue on the left (low) to green in the middle, to red on the right (high). The present output breathing rate of 16 breaths per minute is considered normal, and was originally shown in green.

FIG. 19 shows an example of a graphical breathing rate output. Here the original colors ranged from blue on the left (low) to green in the middle, to red on the right (high). The present output breathing rate of 16 breaths per minute is considered normal, and was originally shown in green.

More General Assessment of a Patient's Respiratory Status
Use of Acoustic Data:

Breathing patterns can be interrupted by audible physiological events such as coughing and sneezing. Breathing patterns can also be distorted by audible physiological problems such as wheezing. This information can be used to provide a more accurate breathing rate assessment, and is of course also valuable in itself as well.

In some embodiments, the invention may also make use of data from cough and respiratory sounds. Such sounds may be captured by various methods, including by use of the previously described oscillometric monitor. This monitor can be additionally equipped with any of an internal or externally mounted microphone array. Additionally, or alternatively, high fidelity acoustic recordings may also be captured through a companion mobile application running on a microphone equipped tablet or smartphone, such as (240).

Here, it is important to distinguish over prior art chest-contact microphone methods such as stethoscopes. Although use of chest-contact microphones is not disclaimed, the invention is particularly focused on non-chest contact methods. Thus here, the audio data generally is not used to determine the breathing rate directly, but instead is used to support the oscillometric respiratory status methods disclosed herein.

Thus, in some embodiments, patient acoustic data can be obtained using one or more patient non-chest-contact microphones. These one or more non-chest-contact microphones can be integrated with the previously discussed limb-mounted oscillometric device. Alternatively, or additionally, these one or more non-chest-contact microphones may be mounted on a smartphone (240) or tablet computer, usually located near the patient. If a smartphone or other device is used, acoustic data from the microphone may be transmitted to the oscillometric device or other device by wireless methods (e.g., Bluetooth, WIFI) or wire transfer (e.g., USB) as desired.

In some embodiments, the system may be configured to transmit the oscillometric pulse wave data to the smartphone (240), tablet computer or other computerized device. In these embodiments, the subsequent analysis may be done using the other device's processor.

According to these embodiments, acoustic recordings of cough and breath sound recordings may then be time-synchronized with the oscillometric sphygmogram and utilized to derive a more accurate and robust respiration rate metric. Supplemental recordings of cough and breathing sounds may also be used to provide diagnostic information for the identification of acute and chronic respiratory illnesses, which could determine dynamic alterations in the average breathing rate algorithm. These average breathing rate algorithm adjustments may include categorical weighting of AM and FM components, updates to artifact removal methods that incorporate variable inhalation and exhalation ratios, and increased tolerances for allowable AM to FM method differential and respiration rate variability.

Put alternatively, in some embodiments, the system may be configured to use at least one non-chest-contact microphone to obtain acoustic data from the patient. The system can then automatically analyze this acoustic data (here using the methods of MacAuslan, or other methods) to determine respiratory interruption signals (such as coughs, wheezing, and the like) and the times these signals occur. The system can then use these respiratory interruption signals and times to perform various subsequent steps. These can include:

Flagging regions of the pulse waveforms as having potential-respiratory-interruption artifacts, and then further editing these waveforms to remove these potential-respiratory-interruption artifacts.

In some embodiments, also modifying the previously discussed function of the AM envelope main harmonic and the FM between-pulse-time main harmonic to further correct for any detected respiratory distress, thereby producing a respiratory-interruption corrected value.

Recording or outputting this respiratory interruption corrected value as the respiratory status of the patient. Additionally, the respiratory interruption indicia or other respiratory distress indicia may also be output as desired.

Methods to Evaluate Breathing Volume and Other Respiratory Conditions

In some embodiments the system may evaluate the amplitudes and durations of the inhalation/exhalation pulses observed in the AM signal and FM signal, and use this evaluation to estimate parameters (such as the volume of air involved) about each inhalation and exhalation cycle.

Figure 20:
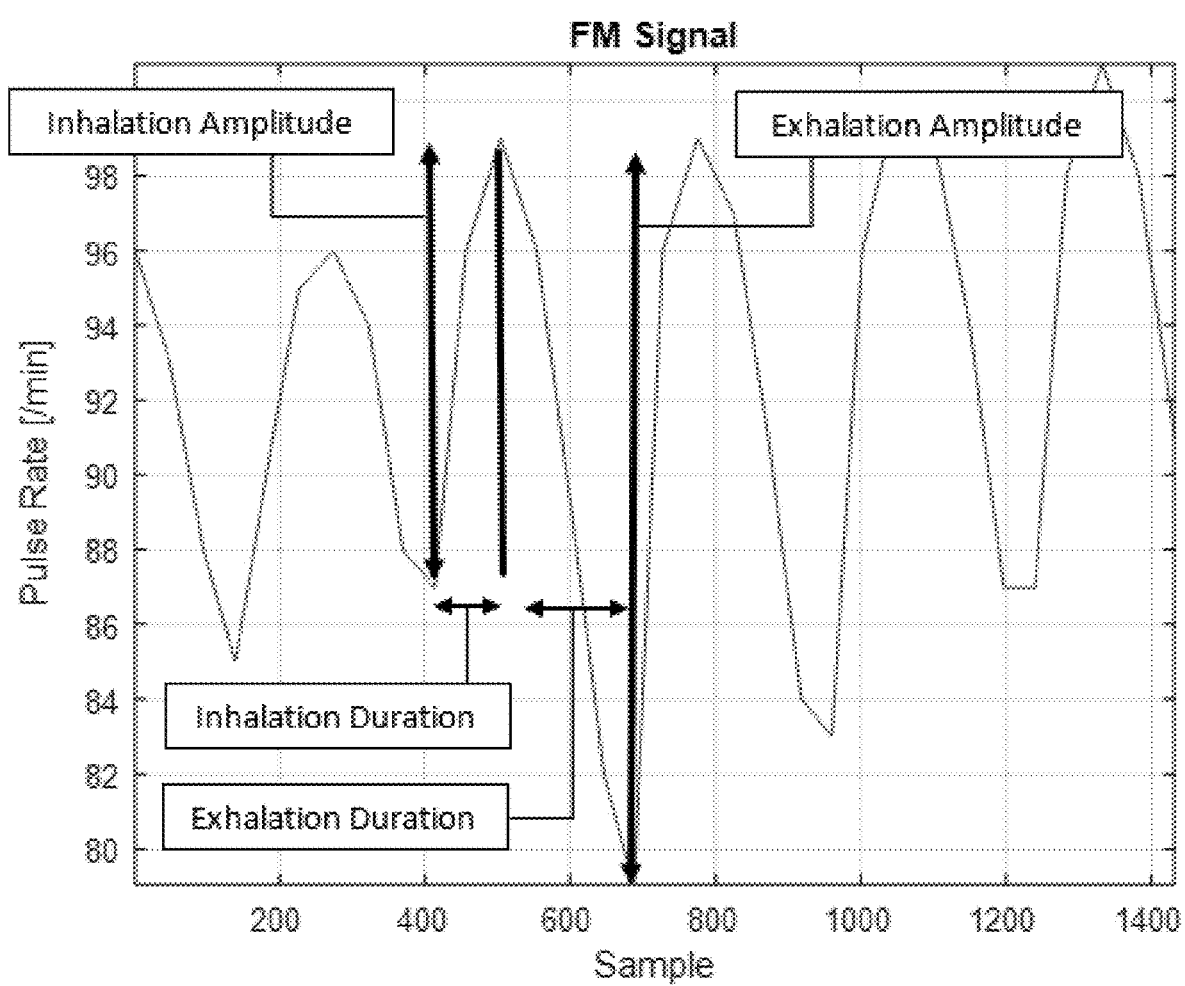
FIG. 20 shows an example of some of the inhalation and exhalation characteristics of an AM breathing signal.
Figure 21:
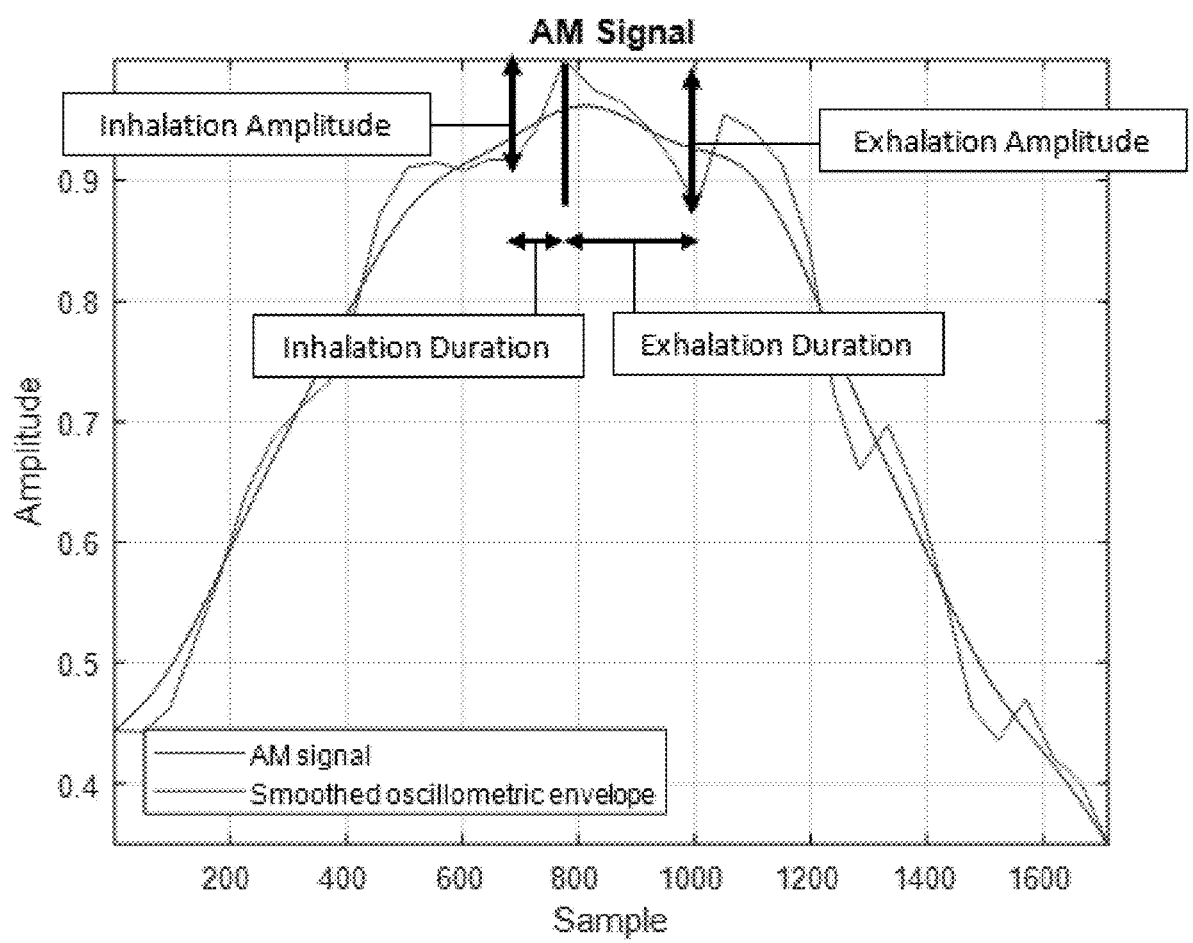
FIG. 21 shows that similarly, in the AM signal, inhalation is represented by the rise in amplitude, while exhalation is represented by the fall in amplitude.

In the FM signal, inhalation is represented by the rise in pulse rate, while exhalation is represented by the fall in pulse rate (see FIG. 20). Similarly, in the AM signal, inhalation is represented by the rise in amplitude, while exhalation is represented by the fall in amplitude (see FIG. 21).

Thus, the time duration per inhalation and exhalation can be calculated from the AM and FM signals. This duration may be used to estimate a metric for instantaneous breathing rates (i.e., breathing rate per inhalation/exhalation). Furthermore, the amplitude per inhalation and exhalation can be calculated from the AM and FM signals. This amplitude may be used to estimate a metric related to instantaneous breathing depth (i.e., shallow or deep breathing per inhalation/exhalation).

This detailed Information about instantaneous breathing rate and instantaneous breathing depth may be used as an indicator of breathing volume and of respiratory conditions, including both chronic and acute conditions such as COPD, asthma, TB, and COVID-19. Such respiratory conditions may have an impact on both the values, ratios, and the patterns of the instantaneous breathing rate and depth observed in a reading, thus providing an indication of a respiratory condition. With this information, the algorithm can be switched between modes that are calibrated to improve performance in the context of certain respiratory conditions. For example, the algorithm may make adjustments to the weighting coefficients, offset, and the ratio of agreement between the AM and FM results in order to optimize performance for a subject that is known to have a respiratory condition, or who exhibits detectable features of a respiratory condition in the AM and FM signals. In some embodiments, audio signals may also be used to help optimize this process.

Thus, in some embodiments, the previously discussed value from the function (comprising the AM envelope main harmonic and the FM between-pulse-time main harmonic) can be used to further analyze the edited pulse waveforms for changes in pulse rate and amplitude due to inhalation and exhalation. Specifically, the one or more processors can compute instantaneous breathing rates during inhalation and exhalation. The system can then use these instantaneous breathing rates and the AM and FM signals to determine either inhalation and/or exhalation volume, and subsequently report this inhalation or exhalation volume as desired. This reporting can be either qualitative (e.g., shallow, average, deep) or quantitative (e.g., liters per minute, tidal volume, etc.).

Furthermore, if the additional modality of breathing sounds is available via a synchronized microphone, the analysis can be extended to include this as well. Such multi-modal analysis can provide improved robustness and reliability of the algorithm. A significant improvement in robustness may be from detection of cough sounds and other respiratory artifacts from the breathing sounds that could be used to improve artifact detection by localizing artifacts in the oscillometric data that impact the AM and FM signals. A significant improvement in reliability may be from improvement of the confidence of the result through agreement between the AM result, FM result, and the respiration rate determined through analysis of breathing sounds. Furthermore, as the breathing sounds employ a different modality than the oscillometric data, artifacts that affect the breathing sounds, such as external audio noise, will have little or no impact on the oscillometric data. Similarly, artifacts that affect the oscillometric data, such as limb movement, will have little or no impact on the breathing sound data. Thus, a combination of the modalities allows greater reliability by improving the result return rate in the presence of noise.

Use for Pain and Stress Measurements

An impartial and quantitative method for non-invasively assessing pain and stress would aid in pain management protocols and combat a growing opioid crisis. The work of Bendall et al., previously discussed, shows that elevated respiratory rate, heart rate, and systolic blood pressure are associated with more severe pain.

In some embodiments, according to the invention, the oscillometric device may be configured to analyze this data and determine when the patient may be experiencing severe pain. For example, the processor may be configured to recognize when the respiration rate is 25 breaths/min or greater, and trigger a "pain" warning flag or notice accordingly.

Other measurements of blood pressure, pulse rate, and average breathing rate, may also be predictive of pain levels. Here the correlation matrix algorithms (which correlate heart rate, respiratory rate, systolic blood pressure, and diastolic pressure vs pain scores) of Bendall J C, et. al." (*Eur J Emerg. Med* 2011 December; 18(6):334-339), or other methods, may be used.

In these embodiments, the system can be configured to further analyze any of the patient's edited pulse waveforms and respiratory status for pain or stress criteria (such as a high breathing rate). The system can further output these pain or stress criteria as pain or stress indicia.

Using these methods, an overall pain assessment metric may be obtained using a regression model that utilizes input features, such as derived vital metrics (e.g., pulse rate, average breathing rate, and blood pressure) and physiological signals (e.g., tri-axial accelerometer and gyroscope, oscillometric sphygmogram signals). Other data, such as of cough and breath sounds, may also be used.

Utility for Early Infectious Disease Detection and Recovery Monitoring

According to the Report of the WHO-China Joint Mission on Coronavirus Disease 2019 (COVID-19), which analyzed 55,924 laboratory confirmed cases, typical signs and symptoms of COVID-19 are: fever (87.9%), dry cough (67.7%), fatigue (38.1%), sputum production (33.4%), shortness of breath (18.6%), sore throat (13.9%), headache (13.6%), myalgia or arthralgia (14.8%), chills (11.4%), nausea or vomiting (5.0%), nasal congestion (4.8%), diarrhea (3.7%), hemoptysis (0.9%), and conjunctival congestion (0.8%) [WHO, 2020].

A retrospective study was conducted utilizing smartwatch data from 5300 participants with 32 participants that contracted COVID-19 [Mishra, 2020]. Results from this study showed that 63% of the COVID-19 cases could have been detected before the onset of reported symptoms, based on significant increases in resting heart rate relative to pre-infection baselines. A subsequent study by Miller et al., analyzed the data collected from a wrist mounted wearable device from 81 subjects who were confirmed positive for COVID-19 and 190 that tested negative. A gradient boosted classifier was trained on metrics derived from the subject's daily respiration rate as compared to pre-symptomatic baseline. This model correctly identified 20% of the patients infected with SARS-CoV-2 two days before the onset of symptoms and was able to identify 80% of all patients infected with SARS-CoV-2 after three days of symptoms.

Blood pressure measurements taken daily with an oscillometric monitor are a non-invasive means of tracking longitudinal vital metrics in populations worldwide. Given the prevalence of a cough and shortness of breath as a symptom of COVID-19, an oscillometric monitor that captures cough and breath sound recording and derives the respiration rate during routine blood pressure measurements, could be utilized for early detection of COVID-19 in patients before symptom onset. Daily measurements allow baseline metrics to be established for respiration rate and pulse rate, and elevated trends identified as indications of SARS-CoV-2 infections. Continued daily monitoring can also be achieved with these vital measurements and patient trajectories predicted for escalating care to an in-patient setting.

As previously discussed, this RRA value can be output either directly as a respiratory rate, or alternatively as a more general respiratory status that may include the respiratory rate along with other breathing related parameters, such as respiratory volume, presence of audible breathing issues (respiratory interruptions such as coughing, wheezing, and the like), and indicia that the system is picking up pain or distress related indicia in the data.

Since audible breathing issues (e.g., respiratory interruptions such as coughing) or possible pain or distress indicia, can impact the accuracy of the results, in some embodiments, it may be useful to also employ alternate types of weighting coefficients, e.g., $a_{1cough}$, $a_{2cough}$, or $a_{1pain}$, $a_{2pain}$ when the system detects evidence of these effects.

The invention claimed is:

1. A method of automatically determining a respiratory status of a patient, said method comprising:
   obtaining pulse waveforms from an oscillometric device mounted on a limb of said patient, said pulse waveforms thus being oscillometric type pulse waveforms;
   analyzing said pulse waveforms, using at least one processor, and determining artifact-free regions of said pulse waveforms, thus obtaining edited pulse waveforms;
   analyzing said edited pulse waveforms, using said at least one processor, and determining AM envelope signals and FM between-pulse-time signals of said edited pulse waveforms;
   analyzing said AM envelope signals and said FM between-pulse-time signals using said at least one processor, and determining an AM envelope main harmonic of said AM envelope signals and an FM between-pulse-time main harmonic of said FM between-pulse-time signals;
   in response to said AM envelope main harmonic and said FM between-pulse-time main harmonic being within a predetermined limit of each other, using said at least one processor to calculate a value from a function comprising said AM envelope main harmonic and said FM between-pulse-time main harmonic;
   and recording or outputting said value as said respiratory status of said patient.

2. The method of claim 1, wherein said oscillometric device further comprises a movement detector device comprising a tri-axial accelerometer and/or a tri-axial gyroscope sensor, wherein said movement detector device reports movement of said oscillometric device to said at least one processor, and said at least one processor further uses said movement to determine at least some of said artifact-free regions of said pulse waveforms.

3. The method of claim 2, wherein said at least some of said artifact-free regions of said pulse waveforms are determined by obtaining oscillometric cuff deflation signals, and analyzing said cuff deflation signals by any of:

a) analyzing areas of said cuff deflation signals where neighboring pulses exhibit below average cross-correlation;
b) automatically deweighting said cuff deflation signals obtained during a time that said movement detector motion detects movement above a preset threshold.

4. The method of claim 1, wherein said at least one processor determines said AM envelope signals by determining an oscillometric envelope of pulse peak amplitudes of said edited pulse waveforms, and determining a time varying amplitude of said AM envelope signals.

5. The method of claim 1, wherein said at least one processor further determines said FM between-pulse-time signals by computing time differences between peak indices of said edited pulse waveforms, and uses these time differences to compute instantaneous pulse rates of said patient;
   and wherein said at least one processor further uses said instantaneous pulse rates to determine said FM between-pulse-time signals.

6. The method of claim 1, wherein said at least one processor determines said AM envelope main harmonic by determining a power spectral density of the main harmonics of an oscillometric envelope of said edited pulse waveform; and
   wherein said at least one processor determines said FM between-pulse-time main harmonic by determining a power spectral density of an instantaneous pulse rate signal that is based on individual pulse positions of the edited pulse waveforms with respect to each other in time.

7. The method of claim 1, further comprising: using said value to further analyze said edited pulse waveforms for changes in pulse rate and amplitude due to inhalation and exhalation;
   using said at least one processor to compute instantaneous breathing rates during said inhalation and exhalation;
   using said instantaneous breathing rates and said AM envelope signals and said FM between-pulse-time signals to determine any of said inhalation and exhalation volume; and
   reporting any said inhalation and exhalation volume along with said respiratory status.

8. The method of claim 1, further comprising: analyzing any of said edited pulse waveforms and said respiratory status of said patient for pain or stress criteria, and further outputting said pain or stress criteria as pain or stress indicia for said patient.

9. The method of claim 1, further comprising: obtaining acoustic data from said patient using at least one non-chest-contact microphone.

10. The method of claim 9, further comprising:
a) analyzing said acoustic data to determine respiratory interruption signals and times;
b) using said respiratory interruption signals and times to perform any of:
   i) flagging regions of said edited pulse waveforms as having potential-respiratory-interruption artifacts, and further editing said waveforms to remove said potential-respiratory-interruption artifacts; and
   ii) modifying said function comprising said AM envelope main harmonic and said FM between-pulse-time main harmonic to correct for a respiratory interruption, thereby producing a respiratory-interruption corrected value; and
recording or outputting said respiratory interruption corrected value as said respiratory status of said patient.

11. A system for automatically determining a respiratory status of a patient, said system comprising:
an oscillometric device configured to be mounted on a limb of said patient, said oscillometric device comprising at least one processor, memory, pressure cuff, and pressure cuff sensor, said oscillometric device configured to obtain pulse waveforms, said pulse waveforms thus being oscillometric type pulse waveforms;
said at least one processor configured to analyze said pulse waveforms, and determine artifact-free regions of said pulse waveforms, thus obtaining edited pulse waveforms;
said at least one processor further configured to analyze said edited pulse waveforms, and determine AM envelope signals and FM between-pulse-time signals of said edited pulse waveforms;
said at least one processor further configured to analyze said AM envelope signals and said FM between-pulse-time signals, and determine an AM envelope main harmonic of said AM envelope signals and an FM between-pulse-time main harmonic of said FM between-pulse-time signals;
said at least one processor configured to determine when said AM envelope main harmonic and said FM between-pulse-time main harmonic are within a predetermined limit of each other, and when within the predetermined limit of each other to calculate a value from a function comprising said AM envelope main harmonic and said FM between-pulse-time main harmonic, and to record or output said value as said respiratory status of said patient.

12. The system of claim 11, wherein said oscillometric device further comprises a movement detector device comprising a tri-axial accelerometer and/or a tri-axial gyroscope sensor, wherein said movement detector device further configured to report movement of said oscillometric device to said at least one processor, and said at least one processor further configured to use said movement to determine at least some of said artifact-free regions of said pulse waveforms.

13. The system of claim 12, wherein said at least one processor is configured to determine said at least some of said artifact-free regions of said pulse waveforms by obtaining oscillometric cuff deflation signals, and analyzing said cuff deflation signals by any of:
a) analyzing areas of said cuff deflation signals where neighboring pulses exhibit below average cross-correlation; and
b) automatically deweighting said cuff deflation signals obtained during a time that said movement detector device detects motion above a preset threshold.

14. The system of claim 11, wherein said at least one processor is further configured to determine said AM envelope signals by determining an oscillometric envelope of pulse peak amplitudes of said edited pulse waveforms, and determine a time varying amplitude of said AM envelope signals.

15. The system of claim 11, wherein said at least one processor is further configured to determine said FM between-pulse-time signals by computing time differences between peak indices of said edited pulse waveforms, and uses these time differences to compute instantaneous pulse rates of said patient;
and wherein said at least one processor further uses said instantaneous pulse rates to determine said FM between-pulse-time signals.

16. The system of claim 11, wherein said at least one processor is configured to determine said AM envelope main harmonic by determine a power spectral density of the main harmonics of an oscillometric envelope of said edited pulse waveform; and
wherein said at least one processor is configured to determine said FM between-pulse-time main harmonic by determining a power spectral density of an instantaneous pulse rate signal that is based on individual pulse positions of the edited pulse waveforms with respect to each other in time.

17. The system of claim 11, wherein said at least one processor is configured to use said value to further analyze said edited pulse waveforms for changes in pulse rate and amplitude due to inhalation and exhalation; and
compute instantaneous breathing rates during said inhalation and exhalation, and use said instantaneous breathing rates and said AM envelope signals and said FM between-pulse-time signals to determine any of inhalation and exhalation volume, and report any of said inhalation and exhalation volume along with said respiratory status.

18. The system of claim 11, wherein said at least one processor is configured to further analyze any of said edited pulse waveforms and said respiratory status of said patient for pain or stress criteria, and output said pain or stress criteria as pain or stress indicia for said patient.

19. The system of claim 11, wherein said at least one processor is configured to further obtain acoustic data from said patient using at least one non-chest-contact microphone.

20. The system of claim 19, wherein said at least one processor is further configured to use said acoustic data to:
a) analyze said acoustic data to determine respiratory interruption signals and times;
b) use said respiratory interruption signals and times to perform any of:
i) flag regions of said edited pulse waveforms as having potential-respiratory-interruption artifacts, and further edit said waveforms to remove said potential-respiratory-interruption artifacts; and
ii) modify said function comprising said AM envelope main harmonic and said FM between-pulse-time main harmonic to correct for a respiratory interruption, thereby producing a respiratory-interruption corrected value; and
record or output said respiratory interruption corrected value as said respiratory status of said patient.

* * * * *